US009585757B2

(12) United States Patent
Slocum, Jr. et al.

(10) Patent No.: US 9,585,757 B2
(45) Date of Patent: Mar. 7, 2017

(54) ORTHOPAEDIC JOINTS PROVIDING ENHANCED LUBRICITY

(71) Applicant: Massachusetts Institute of Technology, Cambridge, MA (US)

(72) Inventors: Alexander H. Slocum, Jr., Huntington, WV (US); Adam T. Paxson, Cambridge, MA (US); Jonathan David Smith, Cambridge, MA (US); Daniel H. Goodman, Boston, MA (US); Kripa K. Varanasi, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/017,178

(22) Filed: Sep. 3, 2013

(65) Prior Publication Data
US 2015/0066152 A1 Mar. 5, 2015

(51) Int. Cl.
*A61F 2/30* (2006.01)

(52) U.S. Cl.
CPC ...... *A61F 2/30767* (2013.01); *A61F 2/30771* (2013.01); *A61F 2002/3084* (2013.01); *A61F 2002/30144* (2013.01); *A61F 2002/30673* (2013.01); *A61F 2002/30838* (2013.01)

(58) Field of Classification Search
CPC .... A61F 2002/30838; A61F 2002/3084; A61F 2002/30673; A61F 2002/30771; A61F 2002/30934; A61F 2/30767
See application file for complete search history.

(56) References Cited

U.S. PATENT DOCUMENTS

| 4,069,933 A | 1/1978 | Newing |
| 4,125,152 A | 11/1978 | Kestner et al. |
| 4,204,021 A | 5/1980 | Becker |
| 4,316,745 A | 2/1982 | Blount |
| 4,503,099 A | 3/1985 | Chang et al. |
| 5,083,606 A | 1/1992 | Brown et al. |
| 5,154,741 A | 10/1992 | da Costa Filho |
| 5,624,713 A | 4/1997 | Ramer |
| 5,853,802 A | 12/1998 | Boyer et al. |

(Continued)

FOREIGN PATENT DOCUMENTS

| CN | 100344341 C | 10/2007 |
| DE | 198 18 956 A1 | 11/1998 |

(Continued)

OTHER PUBLICATIONS

Qin et al., Influence of surface wettability on the tribological properties of laser textured Co—Cr—Mo alloy in aqueous bovine serum albumin soultion, Dec. 26, 2012, Elsevier, Applied Surface Science 268 (2013) pp. 79-86.*

(Continued)

*Primary Examiner* — Brian Dukert
(74) *Attorney, Agent, or Firm* — Choate, Hall & Stewart LLP; William R. Haulbrook; Alexander D. Augst

(57) ABSTRACT

The present disclosure provides, among other things, prosthetic joint components having textured surface(s) for improving lubrication and increasing the useful life of the prosthetic joint components. The textured surface includes solid features configured to stably contain a biological fluid or a synthetic biological fluid therebetween or therewithin for a non-zero residence time.

22 Claims, 19 Drawing Sheets

(56) References Cited

U.S. PATENT DOCUMENTS

| | | | |
|---|---|---|---|
| 5,900,516 A | 5/1999 | Talley et al. | |
| 6,216,472 B1 | 4/2001 | Cathenaut et al. | |
| 6,329,490 B1 | 12/2001 | Yamashita et al. | |
| 7,041,363 B2 | 5/2006 | Krohmer et al. | |
| 7,323,221 B2 | 1/2008 | Heppekausen et al. | |
| 7,458,384 B1 | 12/2008 | Seal et al. | |
| 7,622,197 B2 | 11/2009 | Balow et al. | |
| 7,687,593 B2 | 3/2010 | Yamahiro et al. | |
| 7,722,951 B2 | 5/2010 | Li et al. | |
| 7,985,451 B2 | 7/2011 | Luzinov et al. | |
| 8,235,096 B1 | 8/2012 | Mahefkey et al. | |
| 8,252,259 B2 | 8/2012 | Seal et al. | |
| 8,323,349 B2* | 12/2012 | Schmid | 623/23.58 |
| 8,574,704 B2 | 11/2013 | Smith et al. | |
| 8,859,090 B2 | 10/2014 | Angelescu et al. | |
| 2002/0164443 A1 | 11/2002 | Oles et al. | |
| 2003/0017303 A1 | 1/2003 | Shindo et al. | |
| 2003/0096083 A1 | 5/2003 | Morgan et al. | |
| 2003/0134035 A1 | 7/2003 | Lamb et al. | |
| 2003/0203117 A1 | 10/2003 | Bartkowiak et al. | |
| 2003/0226806 A1 | 12/2003 | Young et al. | |
| 2004/0026832 A1 | 2/2004 | Gier et al. | |
| 2004/0037961 A1 | 2/2004 | Dieleman et al. | |
| 2004/0219373 A1 | 11/2004 | Deruelle et al. | |
| 2004/0243249 A1 | 12/2004 | Ishihara et al. | |
| 2005/0003146 A1 | 1/2005 | Spath | |
| 2005/0009953 A1 | 1/2005 | Shea | |
| 2005/0016489 A1 | 1/2005 | Endicott et al. | |
| 2005/0049716 A1* | 3/2005 | Wagener et al. | 623/23.5 |
| 2005/0061221 A1 | 3/2005 | Paszkowski | |
| 2005/0112326 A1 | 5/2005 | Nun et al. | |
| 2005/0136217 A1 | 6/2005 | Barthlott et al. | |
| 2005/0182494 A1 | 8/2005 | Schmid | |
| 2005/0208272 A1 | 9/2005 | Groll | |
| 2006/0013735 A1 | 1/2006 | Engelking et al. | |
| 2006/0078724 A1 | 4/2006 | Bhushan et al. | |
| 2006/0147675 A1 | 7/2006 | Nun et al. | |
| 2006/0204738 A1 | 9/2006 | Dubrow et al. | |
| 2006/0240218 A1 | 10/2006 | Parce | |
| 2006/0246226 A1 | 11/2006 | Dai et al. | |
| 2007/0031639 A1 | 2/2007 | Hsu et al. | |
| 2007/0135602 A1 | 6/2007 | Yamahiro et al. | |
| 2007/0207335 A1 | 9/2007 | Karandikar et al. | |
| 2007/0231542 A1 | 10/2007 | Deng et al. | |
| 2007/0282247 A1 | 12/2007 | Desai et al. | |
| 2007/0298216 A1 | 12/2007 | Jing et al. | |
| 2008/0085070 A1 | 4/2008 | Hirata et al. | |
| 2008/0118763 A1 | 5/2008 | Balow et al. | |
| 2008/0213461 A1 | 9/2008 | Gill et al. | |
| 2008/0225378 A1 | 9/2008 | Weikert et al. | |
| 2009/0155609 A1 | 6/2009 | Gentleman et al. | |
| 2009/0185867 A1 | 7/2009 | Masters et al. | |
| 2009/0211735 A1 | 8/2009 | Stenkamp et al. | |
| 2009/0231273 A1 | 9/2009 | Lashina et al. | |
| 2010/0028604 A1 | 2/2010 | Bhushan et al. | |
| 2010/0092621 A1 | 4/2010 | Akutsu et al. | |
| 2010/0098909 A1 | 4/2010 | Reyssat et al. | |
| 2010/0112286 A1 | 5/2010 | Bahadur et al. | |
| 2010/0143620 A1 | 6/2010 | Ajdelsztajn et al. | |
| 2010/0147441 A1 | 6/2010 | Nakagawa et al. | |
| 2010/0200094 A1 | 8/2010 | Ermakov | |
| 2010/0218517 A1 | 9/2010 | Luther | |
| 2010/0285229 A1 | 11/2010 | Elbahri et al. | |
| 2010/0285275 A1 | 11/2010 | Baca et al. | |
| 2010/0307922 A1 | 12/2010 | Wu | |
| 2010/0330146 A1 | 12/2010 | Chauhan et al. | |
| 2011/0042850 A1 | 2/2011 | Hong et al. | |
| 2011/0077172 A1 | 3/2011 | Aizenberg et al. | |
| 2011/0106504 A1 | 5/2011 | Noureldin | |
| 2011/0201984 A1 | 8/2011 | Dubrow et al. | |
| 2011/0226998 A1 | 9/2011 | Van De Weijer-Wagemans et al. | |
| 2011/0243650 A1* | 10/2011 | Linares | 403/122 |
| 2011/0283778 A1 | 11/2011 | Angelescu et al. | |
| 2011/0287217 A1 | 11/2011 | Mazumder et al. | |
| 2012/0036846 A1 | 2/2012 | Aizenberg et al. | |
| 2012/0128963 A1 | 5/2012 | Mao et al. | |
| 2013/0003258 A1 | 1/2013 | Xie et al. | |
| 2013/0032316 A1 | 2/2013 | Dhiman et al. | |
| 2013/0034695 A1 | 2/2013 | Smith et al. | |
| 2013/0062285 A1 | 3/2013 | Hoek et al. | |
| 2013/0146536 A1 | 6/2013 | Tarabara et al. | |
| 2013/0220813 A1 | 8/2013 | Anand et al. | |
| 2013/0251769 A1 | 9/2013 | Smith et al. | |
| 2013/0251942 A1 | 9/2013 | Azimi et al. | |
| 2013/0251946 A1 | 9/2013 | Azimi et al. | |
| 2013/0251952 A1 | 9/2013 | Smith et al. | |
| 2013/0333789 A1 | 12/2013 | Smith et al. | |
| 2013/0335697 A1 | 12/2013 | Smith et al. | |
| 2013/0337027 A1 | 12/2013 | Smith et al. | |
| 2014/0147627 A1 | 5/2014 | Aizenberg et al. | |
| 2014/0291420 A1 | 10/2014 | Dhiman et al. | |
| 2015/0125575 A1 | 5/2015 | Smith et al. | |

FOREIGN PATENT DOCUMENTS

| | | |
|---|---|---|
| DE | 100 51 438 A1 | 5/2002 |
| EP | 0230112 A2 | 7/1987 |
| EP | 1892458 A1 | 2/2008 |
| JP | 1 170932 A | 7/1989 |
| JP | 5 240251 A | 9/1993 |
| JP | 2004 037764 A | 2/2004 |
| JP | 2007-278090 A | 10/2007 |
| JP | 2008-223003 A | 9/2008 |
| JP | 2008240910 A | 10/2008 |
| TW | I 233 968 B | 6/2005 |
| WO | WO-93/17077 A1 | 9/1993 |
| WO | WO-99/36490 A1 | 7/1999 |
| WO | WO-02/062568 A2 | 8/2002 |
| WO | WO-03/071275 A1 | 8/2003 |
| WO | WO-2006/017009 A2 | 2/2006 |
| WO | WO-2006/091235 A1 | 8/2006 |
| WO | WO-2007/019362 A1 | 2/2007 |
| WO | WO-2008/111603 A1 | 9/2008 |
| WO | WO-2009/009185 A2 | 1/2009 |
| WO | WO-2009091802 A2 | 7/2009 |
| WO | WO-2010/028752 A1 | 3/2010 |
| WO | WO-2010/082710 A1 | 7/2010 |
| WO | WO-2010/096073 A1 | 8/2010 |
| WO | WO-2010/129807 A1 | 11/2010 |
| WO | WO-2011/087458 A1 | 7/2011 |
| WO | WO-2011/143371 A1 | 11/2011 |
| WO | WO-2012/024099 A1 | 2/2012 |
| WO | WO-2012/100099 A2 | 7/2012 |
| WO | WO-2012/100100 A2 | 7/2012 |
| WO | WO-2013/022467 A2 | 2/2013 |
| WO | WO-2013/130118 A1 | 9/2013 |
| WO | WO-2013/141888 A1 | 9/2013 |
| WO | WO-2013/141953 A2 | 9/2013 |
| WO | WO-2015/034471 A1 | 3/2015 |

OTHER PUBLICATIONS

Bannwart et al., Flow Patterns in Heavy Crude Oil-Water Flow, Journal of Energy Resources Technology, ASME, vol. 126:184-189 (2004).

Buschmann et al., A Molecular Model of Proteoglycan-Associated Electrostatic Forces in Cartilage Mechanics, Journal of Biomechanical Engineering, vol. 117:179-192 (1995).

Cassie et al., Wettability of porous surfaces, Transactions of the Faraday Society, 40: 546-551, (1944).

Chen et al., A Wettability Switchable Surface by Microscale Surface Morphology Change, Journal of Micromechanics & Microengineering, Institute of Physics Publishing, 17(3): 489-195 (2007).

Choi et al., Large Slip of Aqueous Liquid Flow over a Nanoengineered Superhydrophobic Surface, PRL 96:066001 (2006).

Eisenberg et al., Swelling of Articular Cartilage and Other Connective Tissues: Electromechanochemical Forrces, Journal of Orthopaedic Research, vol. 3, Issue 2, pp. 148-159 (1985).

Feng et al., Design and creation of superwetting/antiwetting surfaces. Advanced Materials, 18(23):3063-3078 (2006).

(56) References Cited

OTHER PUBLICATIONS

Gleghorn et al., Lubrication Mode Analysis of Articular Cartilage Using Stribeck Surfaces, Journal of Biomechanics 41:1910-1918 (2008).
Hejazi et al., Wetting Transitions in Two-, Three-, and Four-Phase Systems, Langmuir, 28:2173-2180 (2012).
Heuberger et al., Protein-Mediated Boundary Lubrication in Arthroplasty, Biomaterials 26:1165-1173 (2005).
Hron et al., On the Modeling of the Synovial Fluid, Advances in Tribology, vol. 2010, 12 pages. (2010).
Hupp et al., Experimental Method for Fricitonal Characterization of Micro-Textured Surfaces, Proceedings of TRIB2004: ASME/STLE international Joint Tibology Confrence, pp. 1-6 (2004).
International Search Report, PCT/US2013/057881 mailed on Mar. 7, 2014.
Jaishankar et al., Interfacial Viscoelasticity, Yielding and Creep Ringing of Globular Protein-Surfactant Mixtures, The Royal Society of Chemistry, Soft Matter (2011).
Kavehpour et al., Tribo-Rheometry: From Gap-Dependent Rheology to Tribology, MIT (2003).
Kurtz et al., Prevalence of Primary and Revision Total Hip and Knee Arthroplasty in the United States From 1990 Through 2001, J Bonne Joint Surg Am. 87:1487-1497 (2005).
Lafuma, a. et al., Slippery Pre-Suffused Surfaces; EPL, 96: 56001-p.1-56001-p. 4 (2011).
Lee, J.B. and Lee, S.H., Dynamic Wetting and Spreading Characteristics of a Liquid Droplet Impinging on Hydrophobic Textured Surfaces, Langmuir, 27:6565-6573 (2011).
Li, X. et al., Dynamic Behavior of the Water Droplet Impact on a Textured Hydrophobic/Superhydrophobic Surface: The Effect of the Remaining Liquid Film Arising on the Pillars' Tops on the Contact Time, Langmuir, 26(7):4831-4838 (2010).
Mazzucco et al., Rheology of Joint Fluid in Total Knee Arthroplasty Patients, Journal of Orthopaedic Research 20:1157-1163 (2002).
Mishina et al., Changes in Human Serum Albumin on Arthroplasty Frictional Surfaces, Wear 265:655-663 (2008).
Onda et al., Super-water-repellent fractal surfaces. Langmuir, 12(9) (1996).
Pozzato, A. et al., Superhydrophobic surfaces fabricated by nanoimprint lithography, Microelectronic Engineering, 83:884-888 (2006).
Quéréet al., Surfing the hot spot. Nature Materials, 5(6):429-430 (2006).
Quéré, D., Leidenfrost dynamics, Annu. Rev. Fluid Mech., 197-215 (2013).
Quérée, D., Non-sticking drops, Institute of Physics Publishing, Rep.Prog.Phys., 68(11):2495-2532 (2005).
Reyssat et al., Dynamical superhydrophobicity. Faraday Discussions, 146:19-33 (2010).
Reyssat, et al., Bouncing transitions on microtextured materials. Europhysics Letters, 74(2):306-312 (2006).
Roba et al., The Absorpotion and Lubrication Behavior of Synovial Fluid Proteins and Glycoproteins on the Bearing-Surface Materials of Hip Replacements, Biomaterials, vol. 20:2072-2078 (2009).
Schmidt et al., Effect of Synovial Fluid on Boundary Lubrication of Articular Cartilage, OsteoArthritis and Cartilage 15:35-47 (2007).
Seiwert et al., Coating of a Textured Solid, J. Fluid Mech., 2011, 669: 55-63.
Seiwert et al., Drainage on a Rough Surface, EPL 94:16002 (2011).
Sekeroglu et al., Transport of a soft cargo on a nanoscale ratchet. Applied Physics Letters, 99(6) (2011).
Sharma et al., Rheology of Globular Proteins: Apparent Yield Stress, High Shear Rate Viscosity and Interfacial Viscoclasticity of Bovine Serum Albumin Solutions, The Royal Society of Chemistry 2011, Soft Matter, 11 pages. (2011).
Smith et al., Droplet Mobility on Lubricant-Impregnated Surfaces, Soft Matter, 2012(9): 1772-1780 (2012).
Smith et al., Liquid-encapsulating surfaces: overcoming the limitations of superhydrophobic surfaces for robust non-wetting and anti-icing surfaces. in Bulletin of the American Physical Society (2011) Abstract Only.
Song et al., Superhydrophobic Surfaces Produced by Applying a Self-Assembled Monolayer to Silicon Micro/Nano-Textured Surfaces, Nano Research, 2009, 2: 143-150.
Tandon et al., A New Model for Synovial Joint Lubrication, International Journal of Bio-Medical Computing (1993).
Tuteja et al., Designing superoleophobic surfaces. Science, 318(5856):1618-1622 (2007).
Tuteja et al., Robust omniphobic surfaces. Proceedings of the National Academy of Sciences of the United States of America, 105(47):18200-18205 (2008).
Wenzel, Resistance of Solid Surfaces to Wetting by Water, Industrial & Engineering Chemistry, 28(8): 988-994 (1936).
Wong et al., Bioinspired Self-Repairing Slippery Surfaces with Pressure-Stable Omniphobicity, Nature, 477(7365):443-447 (2011).
Written Opinion, PCT/US2013/057881 mailed on Mar. 7, 2014.
Allain et al., A New Method for Contact-Angle Measurements of Sessile Drops, Journal of Calloid and Interface Science, vol. 107, No. 1, Sep. 1985, 9 pages.
Anand et al., Enhanced Condensation on Lubricant-Impregnated Nanotextured Surfaces. ACS Nano, 6(11):10122-10129 (2012).
Blossey, R., Self-cleaning surfaces—Virtual realities. Nature Materials, 2(5):301-306 (2003).
Chandra et al., Observations of droplet impingement on a ceramic porous surface. International Journal of Heat and Mass Transfer 35(10):2377-2388 (1992).
Chaudhuri et al., Dynamic Contact Angles on PTFE Surface by Aqueous Surfactant Solution in Absence and Presence of Electrolytes, Journal of Colloid and Interface Science, 337:555-562 (2009).
Deng, T. et al., Nonwetting of impinging droplets on textured surfaces, Applied Physics Letters, 94(13):133109 (2009).
Fondecave, R. and Wyart, F.B., Polymers as Dewetting Agents, Marcomolecules 31:9305-9315 (1998).
Fujimoto et al., Deformation and rebounding processes of a water droplet impinging on a flat surface above Leidenfrost temperature. Journal of Fluids Engineering, Transactions of the ASME, 118(1):142-149 (1996).
Furmidge, Studies at Phase Interfaces, Journal of Colloid Science, 1962, 17: 309-324.
Gao et al., Artificial lotus leaf prepared using a 1945 patent and a commercial textile. Langmuir, 22(14):5998-6000 (2006).
Good, Robert J., Contact angle, wetting and adhesion: a critical review, J. Adhesion Sci. Technol. vol. 6, No. 12, pp. 1269-1302 (1992).
International Search Report and Written Opinion, PCT/US2011/061498, Jul. 31, 2012, 17 pages.
International Search Report, PCT/US2011/061898, Apr. 24, 2013, 6 pages.
International Search Report, PCT/US2012/030370, Oct. 15, 2012, 6 pages.
International Search Report, PCT/US2012/042326, Dec. 3, 2012, 4 pages.
International Search Report, PCT/US2012/042327, May 16, 2013, 6 pages.
International Search Report, PCT/US2013/021558, Oct. 11, 2013, 5 pages.
International Search Report, PCT/US2013/028439, Dec. 5, 2013, 6 pages.
International Search Report, PCT/US2013/042771, May 26, 2014, 4 pages.
International Search Report, PCT/US2013/045731, Nov. 12, 2013, 3 pages.
International Search Report, PCT/US2013/070827, Mar. 27, 2014, 7 pages.
Kim et al., Hierarchical or not? Effect of the length scale and hierarchy of the surface roughness on omniphobicity of lubricant-infused substrates. Nano Letters, 13(4):1793-1799 (2013).
Liu et al., Metallic Surfaces with Special Wettability, Nanoscale, 3:825-238 (2011).

(56) References Cited

OTHER PUBLICATIONS

Mishchenko et al., Design of ice-free nanostructured surfaces based on repulsion of impacting water droplets. ACS Nano, 4(12):7699-7707 (2010).
Park et al., A Numerical Study of the Effects of Superhydrophobic Surface on Skin-Friction Drag in Turbulent Channel Flow, Phys. Fluids 25, 110815 (2013).
Rausch et al., On the Characteristics of Ion Implanted Metallic Surfaces Inducing Dropwise Condensation of Steam, Langmuir, 26(8): 5971-5975 (2010).
Rothstein, J. P., Slip on superhydrophobic surfaces, ANRV400-FL42-05, ARI, 89-109.
Rykaczewski et al., Mechanism of Frost Formation of Lubricant-Impregnated Surfaces, Langmuir 2013, 29 5230-5238, 13 pages.
Santos et al., Modified Stainless Steel Surfaces Targeted to Reduce Fouling, J. Food Engineering, 64:63-79 (2004).
Tropmann et al., Completely Superhydrophobic PDMS Surfaces for Microfluidics, Langmuir, ACS Publications (2012).
Varanasi et al., Spatial Control in the Heterogeneous Nucleation of Water, Applied Physics Letters, 95: 094101-01-03 (2009).
Varanasi, K.K. et al., Frost formation and ice adhesion on superhydrophobic surfaces, Applied Physics Letters, 97(23):234102 (2010).
Written Opinion, PCT/US2011/061898, Apr. 24, 2013, 9 pages.
Written Opinion, PCT/US2012/030370, Oct. 15, 2012, 10 pages.
Written Opinion, PCT/US2012/042326, Dec. 3, 2012, 7 pages.
Written Opinion, PCT/US2012/042327, May 16, 2013, 6 pages.
Written Opinion, PCT/US2013/021558, Oct. 11, 2013, 7 pages.
Written Opinion, PCT/US2013/028439, Dec. 5, 2013, 11 pages.
Written Opinion, PCT/US2013/042771, May 26, 2014, 7 pages.
Written Opinion, PCT/US2013/045731, Nov. 12, 2013, 3 pages.
Written Opinion, PCT/US2013/070827, Mar. 27, 2014, 15 pages.

\* cited by examiner

ORTHOPAEDIC JOINTS PROVIDING ENHANCED LUBRICITY

GOVERNMENT SUPPORT

This invention was made with Government support under Contract No. W81XWH-09-2-0001, awarded by the U.S. Army Medical Research and Material Command. The Government has certain rights in the invention.

TECHNICAL FIELD

This invention relates generally to articles, devices, and methods for enhancing lubrication of prosthetic joints. More particularly, in certain embodiments, the invention relates to articles, devices, and methods for improving lubrication of prosthetic joints by application of a textured prosthetic joint surface.

BACKGROUND

Lubrication is exceedingly important in prosthetic joints. Lubrication enables sliding motion between the prosthetic joints, which are often used to improve synovial and other joints.

The most common total joint replacements occur at the hip and the knee as discussed in Kurtz, S., Mowat, F., Ong, K., Chan, N., Lau, E., Halpern, M., "Prevalence of Primary and Revision Total Hip and Knee Arthroplasty in the United States from 1990 Through 2002," Journal of Bone and Joint Surgery, July 2005, Vol. 87A:7, pp. 1487-1496. A combination of limited prosthesis lifetime, an increasingly aging population, and the fact that more patients are receiving joint replacements at a younger age necessitate investigation of improvements to joint performance on all fronts. Current thrusts in joint research are focused in the fields of materials science and materials selection, mechanical component design, and improving lubricity of prosthesis components when bathed in synovial fluid. Orthopaedic alloys used for prostheses currently include Cobalt-Chrome (CoCr), Stainless Steel, Titanium, and Cross-Linked Ultra-High Molecular Weight Poly-Ethylene (UHMWPE), as discussed in Revel, P. A., Ed., "Joint Replacement Technology," (2008), Woodhead Publishing, Ltd., Cambridge, UK.

When implanted into a patient, lubrication is provided by synovial fluid, an ultrafiltrate of blood plasma containing proteins, phospholipids, lubricin, and other molecules which affect normal lubrication regimes and give synovial fluid its shear-thinning, non-Newtonian properties. Synovial fluid is produced by the synovial membrane in the joint capsule. Denaturation of synovial fluid proteins, primarily albumin, has been attributed to increased friction and heat generated at the metal/polymer interface, as discussed in Mishina, H., Kojima, M., "Changes in Human Serum Albumin on Arthroplasty Frictional Surfaces," Wear, 256:655-663, 2008. The increased friction and heat generation result in increased wear, and have the overall effect of decreasing the useful life of prosthetic joints. In bovine synovial fluid, Bovine Serum Albumin (BSA) is the most abundant protein. It is also, by convention and because it is readily available and relatively consistent in formulation, the most common lubricant used for tribological testing of orthopaedic materials. Denatured albumin preferentially adsorbs onto hydrophobic surfaces and forms a compact, passivating layer that increases sliding friction leading to increased shear stress and greater wear, as discussed in Heuberger, M. P., Widmer, M. R., Zobeley, E., Glockshuber, R., Spencer, N. D., "Protein-mediated boundary lubrication in arthroplasty," Biomaterials, 26:1165-1173, 2005 and in Roba, M., Naka, M., Gautier, E., Spencer, N. D., Crockett, R., "The Adsorption and Lubrication Behavior of Synovial Fluid Proteins and Glycoproteins on the Bearing-Surface Materials of Hip Replacements," Biomaterials, 30:2072-2078, 2009. Glycoproteins present in synovial fluid adsorb onto the hydrophobic polymer surfaces by way of their hydrophobic backbone, presenting their hydrophilic side chains to form a hydrated boundary layer on the surface of the polymer. As such, due to the wide range of proteins found in synovial fluid, and the variability in surface chemistry of the implants, there are significant challenges associated with improving lubrication on the molecular level.

Fluorescence microscopy and gel electrophoresis have been used to investigate the ability of glycoproteins to adsorb onto UHMWPE and alumina in the presence of other synovial fluid proteins. The wide range of proteins present in synovial fluid, including albumin, glycoproteins, proteoglycans, and glycosaminoglycans (GAGs), should be included in any tribo-rheological characterization of nano- or micro-engineered coatings. Using synovial fluid in experiments may facilitate the prediction of the behavior of the surfaces in relation to in-vivo lubrication. Models of normal articulating joint lubrication suggest that a lubricating gel is formed from thickly concentrated hyaluronic acid molecules, which acts as a boundary lubricant preventing cartilage-to-cartilage contact very briefly during gait cycles, as discussed in Tandon, P. N., Bong, N. H., Kushwaha, K., "A New Model for Synovial Joint Lubrication," International Journal of Bio-Medical Computing, 35:2, 125-140, 1994. A similar boundary layer is formed in a joint prosthesis from both normal and denatured proteins. Polymers are not good conductors of thermal energy, and, if a polymer bearing insert is used, as in a total knee replacement, this can result in heating and micro-melting at any points of contact where increased friction is observed due to denatured protein adsorption. This results in further increases to the rate of protein denaturation, and could suggest one mechanism leading to increased wear of the hydrophobic surface of the polymer.

There is a need for new and improved prosthetic joint components with extended useful life.

SUMMARY OF THE INVENTION

In some embodiments, the invention relates to prosthetic joints with improved surface lubricity due to textures with nano- and/or micro-scale solid features that encapsulate biologic fluid (or synthetic thereof) therebetween or therewithin. Improving the lubricity of a surface aids in prolonging the useful lifetime and minimizing the wear of the prosthetic joint. Modifying the macro-scale surface chemistry improves surface wetting, such that the macro-scale features will encapsulate the water-based lubricant fluid and support the formation of lubrication regimes that minimize wear of the prosthetic joint or implant. One lubrication regime that minimizes wear of a prosthetic joint or implant is hydrodynamic lubrication.

The current disclosure relates to lubrication of metallic surfaces for orthopaedic implants using nano- and or micro-texturing. In some embodiments, nano- and/or micro-texturing is achieved via etching with NaOH. In other embodiments, nano- and/or micro-texturing is achieved via other suitable methods configured to achieve comparable results to etching with NaOH, such as electrochemical treatment with phosphoric acid and DC current.

Three lubrication regimes include boundary layer, hydrodynamic, and elastohydrodynamic lubrication regimes. It is found that boundary layer lubrication leads to the most wear. Application of a nano- and/or micro-texture to the normally hydrophilic surfaces of components in relative motion enables the components to act as super-hydrophilic. These super-hydrophilic components then can encapsulate fluid by action of capillary-like forces. At this length scale, capillary-like forces dominate and can be used to ensure that a layer of fluid is always present on the surface of the material and held (encapsulated) within the solid features of the surface of the material. In this way, the material becomes "self-lubricating." Synovial fluid surrounds the material and acts as both the encapsulating liquid and the free-flowing phase; thus, some embodiments presented herein employ a one phase system to provide continuous lubrication of the joints.

According to certain embodiments, application of this texture to the metallic surfaces of orthopaedic implants can lead to reduced component wear. In some embodiments, the adjacent part(s) include a hip ball and socket joint, or a knee joint with femoral and tibial components. The application of the texture described in certain embodiments presented herein results in increased prosthesis lifetimes and improved patient outcomes as compared to conventional prosthetic joints.

According to one aspect presented herein, a prosthetic joint includes a first joint component and a second joint component. The first joint component is positioned in relation to the second joint component such that it is separated from the second joint component by a gap throughout a range of motion of the first joint component in relation to the second joint component. The gap has a thickness that varies according to position within the range of motion of the first joint component in relation to the second joint component. The first joint component includes a first surface opposing the second joint component. The first surface has a first texture including solid features configured to stably contain a biological fluid or a synthetic biological fluid therebetween or therewithin for a non-zero residence time.

According to another aspect presented herein, a prosthetic joint includes a first joint component. The first joint component includes a first surface. The first surface has a first texture including solid features configured to stably contain a biological fluid or a synthetic biological fluid therebetween or therewithin for a non-zero residence time.

In some embodiments, the biological fluid or the synthetic biological fluid is synovial fluid. In some embodiments, the biological fluid or the synthetic biological fluid includes at least one fluid selected from mucus, blood, blood products, saliva, lacrimal fluid, bovine serum, human serum, secretion, semen, cerebrospinal fluid (CSF), plasma, bile, bodily fluids, any biological fluid(s) including a suspended protein, and any combination of the above-mentioned fluids.

In some embodiments, the first surface has a contact angle with water of ≤50°. In some embodiments, the first surface has a skew value of less than 0 (zero). In some embodiments, the solid features of the first texture define pores. In some embodiments, the pores have an average dimension of between 10-500 nanometers. In some embodiments, the pores have an average dimension of between 1-500 microns. In some embodiments, the first texture comprises micro- and/or nano-features, configured to encapsulate the biological fluid or the synthetic biological fluid for the residence time. In some embodiments, the micro- and/or nano-features form a honeycomb structure or a foam mesh. In some embodiments, the residence time is between 5 seconds and 40 seconds. In some embodiments, the first texture is an etched surface, an anodized surface, or a surface treated chemically or electro-chemically to induce formation of nano- or micro-features.

In some embodiments, the second joint component includes a second surface, the second surface opposing the first surface, the second surface being smooth. In some embodiments, the second joint component comprises a second surface, the second surface opposing the first surface, the second surface having a second texture including solid features. In some embodiments, the second texture is an etched surface, an anodized surface, or a surface treated chemically or electro-chemically to induce formation of nano- or micro-features. In some embodiments, the solid features of the second texture define pores or structures capable of encapsulating fluids for the residence time. In some embodiments, the prosthetic joint is configured to support formation of a hydrodynamic lubrication regime and to maintain said hydrodynamic lubrication regime between the first and the second joint components. In some embodiments, the prosthetic joint is configured to modify the shear stress and friction between the first component and the second component to improve lubrication between the first component and the second component.

In some embodiments, the prosthetic joint is configured to reduce the shear stress by more than about 50% as compared to an analogous prosthetic joint with the first surface and the second surface being smooth. In some embodiments, the first surface, the second surface, or the first surface and the second surface, include a metal, a metal alloy, a polymer, a ceramic, a metal polymer, or any combination thereof. In some embodiments, the first surface, the second surface, or the first surface and the second surface, include Ti—Zr, Ti-6Al-4V, Ti-6Al-7Nb, Ti-5Al-2.5Fe, Ti-3Al-2.5V, Ti-13Nb-13Zr, Ti-15Mo-5Zr-3Al, Ti-12Mo-6Zr-2Fe, Ti-15Mo-2.8Nb-3Al, Ti-35Nb-5Ta-7Zr(TNZT), Ti-15Mo-2.8Nb-0.2Si-0.3O, Ti-35Nb-5Ta-7Zr-0.4O, Ti-15Mo, Ti-16Nb-10Hf, CPTi (>>98% Ti), Co—Cr—Mo, Co—Cr alloys, Stainless Steel 316L, and any combination thereof.

In some embodiments, the gap height between the first component and the second component is between 10 microns and 1 millimeter. In some embodiments, the first texture is a coating. In some embodiments, the first texture is not a coating.

BRIEF DESCRIPTION OF THE DRAWINGS

The objects and features of the invention can be better understood with reference to the drawings described below, and the claims.

FIG. 13(a) shows a conical clamp (center) used to fix the base to the rheometer. FIG. 13(b) shows a bottom sample on a kinematic coupling and an upper sample fixed to the machine's rotating spindle. FIG. 13(c) shows a detail view of the kinematic coupling and accompanying flexural support.

FIG. 15 demonstrates a reduction in stress achieved when an anodized coating, lubricated with synovial fluid, is in contact with a smooth surface (giving a known boundary condition for one side of the flow).

DESCRIPTION

Figure 1:
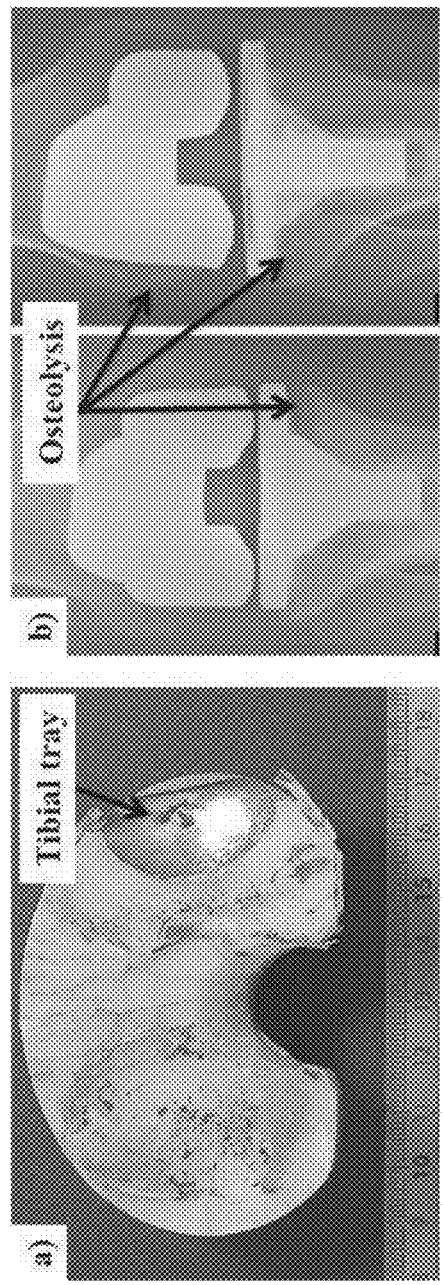
FIG. 1(a) shows an image of a severely worn polymer insert from a prosthetic knee joint. The polymer insert has been worn through down to the underlying tibial tray support.
FIG. 1(b) is a radiograph showing periprosthetic osteolysis most likely induced by wear of joint materials and release of particles.

It is contemplated that apparatus, articles, methods, and processes of the claimed invention encompass variations and adaptations developed using information from the embodiments described herein. Adaptation and/or modification of the apparatus, articles, methods, and processes described herein may be performed by those of ordinary skill in the relevant art.

Throughout the description, where apparatus and articles are described as having, including, or comprising specific components, or where processes and methods are described as having, including, or comprising specific steps, it is contemplated that, additionally, there are apparatus and articles of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

In certain embodiments, micro-scale features are used (e.g., from about 50 microns to 400 microns in characteristic dimension). In certain embodiments, the micro-scale features are from about 1 to about 500 microns in characteristic dimension, including between 1-10 microns, 1-20 microns, 1-50 microns, 50-100 microns, 100-200 microns, 200-300 microns, 300-400 microns, or 400-500 microns in characteristic dimension. In certain embodiments, nano-scale features are used (e.g., features less than 1 micron, e.g., between about 1 nm to about 1 micron). In some embodiments, the nano-scale features are from about 1 to about 500 nm in characteristic dimension, including between 1-10 nm, 1-20 nm, 1-50 nm, 50-100 nm, 100-200 nm, 200-300 nm, 300-400 nm, 400-500 nm in characteristic dimension. In certain embodiments, the micro- and/or nano-scale features form a honeycomb structure or a foam mesh.

There are two interfaces in prostheses that are critical to the implant's long-term success: the implant-implant interface and the implant-bone interface. An implant's durability and useful lifetime can be increased by application of porous coatings at each of these interfaces to promote ingrowth of bone and improve lubrication between implant components in contact. On one hand, characteristics of the implant-bone interfaces determine the degree of bone growth into the coating, influencing the subsequent integrity of a relatively rigid prosthesis-bone joint. On the other hand, lubrication between two opposing surfaces in an implant (the implant-implant interface) directly affects wear in the prosthesis and in turn determines the lifetime of the joint. Lubrication is especially important, however, based on empirical observation of current joints, as wear of joint components can have a significant negative effect on the implant/bone interface—e.g., periprosthetic osteolysis.

The importance of lubrication and integration in an implant is illustrated in FIG. 1(a), which shows a severely worn polymer insert from a prosthetic knee joint, and a radiograph highlighting the osteolysis that can result, as shown in FIG. 1(b). These images, shown in FIG. 1, are representative and are not from the same patient. They highlight the potential morbidity associated with fatigue and fracture of the polymer bearing, and subsequent release of micron and sub-micron scale particles from both the polymer and metallic components. This pathologic process leads to up-regulation of osteoclast activity and greater rates of bone degradation (periprosthetic osteolysis), otherwise known as aseptic loosening.

Increasing hydrophilicity of a metallic joint surface supports adsorption of normal synovial fluid (synovial fluid) proteins. Also, a hydrophilic surface significantly mitigates the amount of adsorption of those proteins which become denatured. Denatured proteins tend to have negative effects on formation of a boundary layer in joints during use. The adsorption of native hydrophilic proteins is driven by Van der Waals forces; native proteins also form a thicker boundary film because their hydrophilic moieties remain more hydrated by synovial fluid than would those of denatured, hydrophilic proteins. Certain embodiments relate to improving lubrication of implant surfaces to help decrease wear rates, resulting in increased implant lifetime and improved patient outcomes. Some embodiments may achieve a 50% or more increase in the lifetime of the implant due to the reduced wear stress. Thus, in some embodiments, a joint with a working lifetime of 20 years could last 30 years if the wear stresses in the joint were reduced by 50% (lifetime improves by 50%), with all other factors being equal. Even modest reductions in shear stress by 20 or 30% could result in several more years of viable joint lifetime, which in turn results in significant cost savings—e.g., savings in raw materials because implants do not have to be reduced as often, overall reduction in healthcare costs due to the lower frequency of implant replacement, reduction in doctors' and other hospital staff time expenditures (e.g., because implants do not have to be replaced as often), and improved patient outcomes (e.g., the ability to wear the implant for a longer period of time without the need for a replacement).

Figure 2:
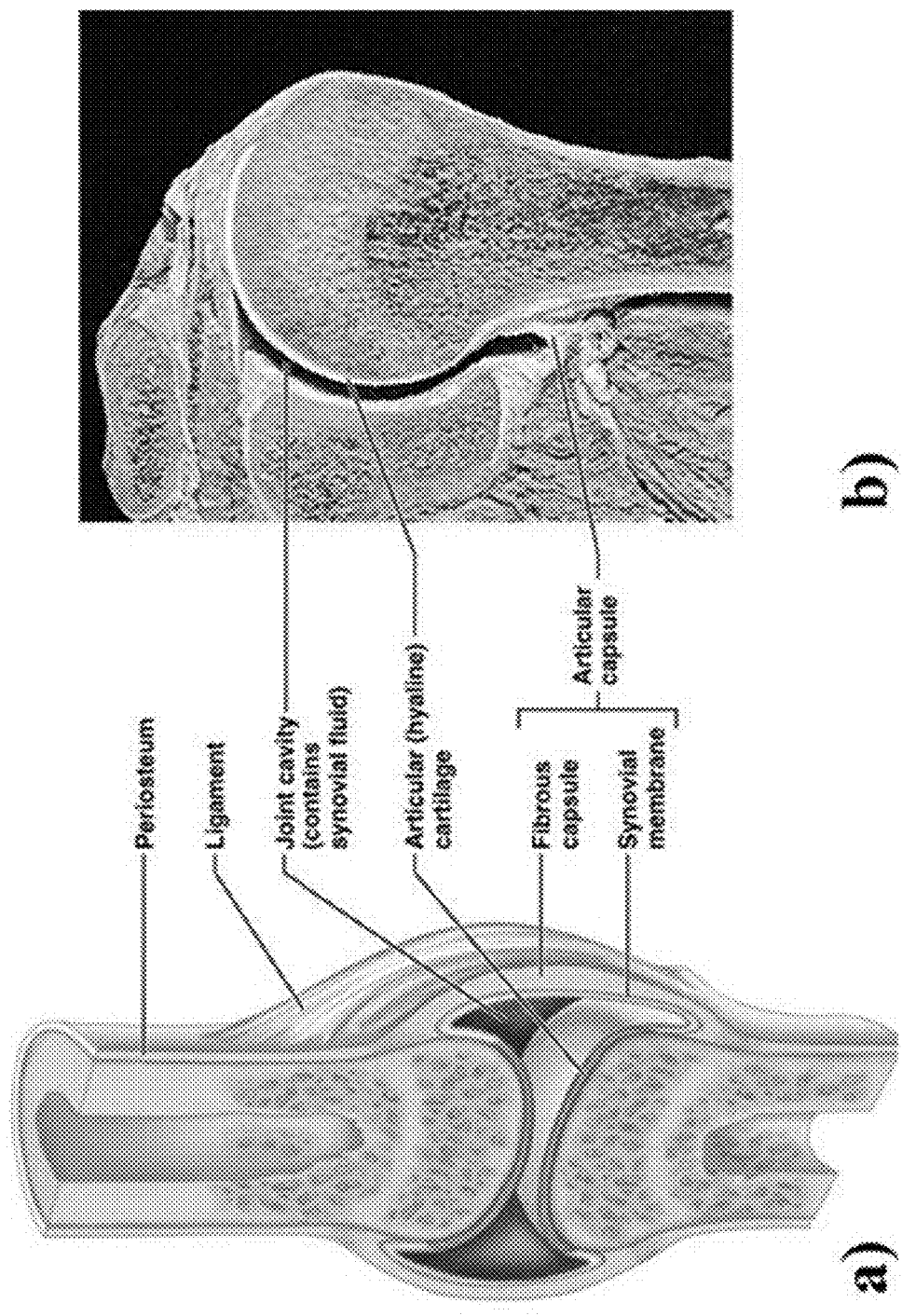
FIG. 2(a) is a schematic of a synovial joint and FIG. 2(b) is a cross-section of the gleno-humeral (shoulder) joint, showing a thin layer of hyaline cartilage and articular capsule.

Lubrication enables sliding motion between joint components, which are often used to replace synovial joints. FIG. 2 shows examples of synovial joints, which are lubricated by synovial fluid, which is a water-based lubricant produced by the synovial membrane surrounding the articular capsule. When a prosthesis replaces a diseased or damaged synovial joint, the joint capsule is usually preserved and the prosthesis subsequently becomes bathed in synovial fluid in the same manner as the biological joint. The synovial fluid constantly surrounds the prosthesis. As discussed above, wear of the joint components leads to significant morbidity through periprosthetic osteolysis. Improvements to lubrication in a prosthetic joint can lessen the rate of wear of joint components, leading to increased joint lifetimes and improved outcomes.

Although synovial fluid is discussed primarily throughout the specification, those of ordinary skill in the art would appreciate that certain embodiments relate to improving lubrication of prosthetic joints where the encapsulating fluid and the flowing fluid is at least one of synovial fluid, mucus, blood, blood products (including synthetics), saliva, lacrimal fluid (tears), bovine serum, human serum, secretion, semen, cerebrospinal fluid (CSF), plasma, bile, bodily fluids, any biological fluid(s) including a suspended protein, synthetic versions of any of the above-mentioned fluids, and any combination of the above-mentioned fluids.

Porous coatings are unique in that when the coating is fabricated from a material that is non-wetting or only slightly wetting (like smooth titanium), the resulting porous surface is usually far more wetting, as will be discussed further below. This is important because a coating can be used to stabilize a water-based lubricant at the surface of the implant, as discussed in Smith, J. D., Dhiman, R., Anand, S., Garduno, E. R., Cohen, R. E., McKinley, G. H., Varanasi, K. K., "Droplet Mobility on Lubricant-Impregnated Surfaces," Soft Matter (Accepted) and Anand, S., Paxson, A. T., Dhiman, R., Smith, J. D., Varanasi, K. K., "Enhanced Condensation on Lubricant-Impregnated Nanotextured Surfaces," *ACS Nano,* 2012 6 (11), pp. 10122-10129, which are incorporated herein by reference in their entirety. Joints already have a lubricant present; synovial fluid is 98% water and the other 2% are proteins like albumin and lubricin. Thus, a wetting surface will encapsulate the synovial fluid and prevent "squeeze out" when two surfaces are brought into close contact, as often occurs in prosthetic joints. This process is also assisted significantly by the micro-structure of articular cartilage; in a way, the porous coating is designed to act as artificial cartilage. In some embodiments, to lubricate a prosthetic joint with a porous coating, only a single fluid should be encapsulated as risks associated with a pre-impregnated fluid leaking out are too high, as discussed in Smith, J. D., Dhiman, R., Anand, S., Garduno, E. R., Cohen, R. E., McKinley, G. H., Varanasi, K. K., "Droplet Mobility on Lubricant-Impregnated Surfaces," *Soft Matter* (*Accepted*) and Anand, S., Paxson, A. T., Dhiman, R., Smith, J. D., Varanasi, K. K., "Enhanced Condensation on Lubricant-Impregnated Nanotextured Surfaces," *ACS Nano,* 2012 6 (11), pp. 10122-10129, as well as the risk to the patient in needing to replenish impregnated fluid through injection or other methods. In some embodiments, the present invention could be utilized with pre-impregnated fluids (e.g., fluids impregnated into the surface prior to introducing the implant into the patient) if used in an environment where replenishment of the impregnated fluid would pose no risk to the patient.

Figure 3:
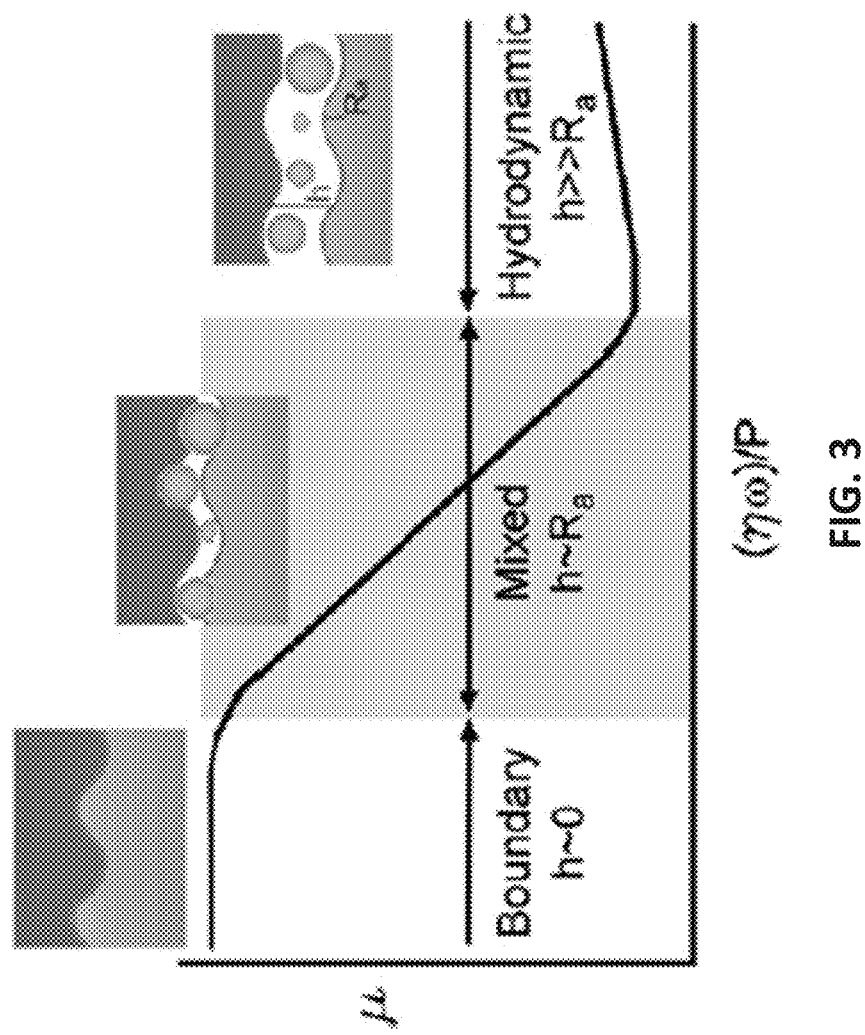
FIG. 3 shows a curve of three different types of lubrication present in synovial joints.

There are three principle types of lubrication regimes present in synovial joints, illustrated by the Stribeck Curve in FIG. 3. As discussed above, the three lubrication regimes generally known are boundary, mixed, and hydrodynamic lubrication. When an individual is at rest, their joints settle, much like a journal bearing, and when they start moving, boundary layer lubrication is present. In the native joint, this is dominated by the surface chemistry of articular cartilage.

Boundary lubrication has been found to be the dominant factor leading to wear of artificial joint bearing components, as discussed in Gleghorn, J. P., Bonassar, L. J., "Lubrication Mode Analysis of Articular Cartilage Using Stribeck Surfaces," Journal of Biomechanics, 2008, Vol. 41, pp. 1910-1918. As motion continues, hydrodynamic forces increase, leading to eventual formation of a hydrodynamic lubrication regime and separation of the joint components by a fluid gap. The dynamics of synovial joint lubrication are made even more complicated by the fact that the lubricant, synovial fluid, is shear-thinning; thus, as the shear rate increases, the viscosity will decrease, as discussed in Sharma, V., Jaishankar, A., Wang, Y.-C., McKinley, G. H., "Rheology of Globular Proteins: Apparent Yield Stress, High Shear Rate Viscosity and Interfacial Viscoelasticity of Bovine Serum Albumin Solutions," Soft Matter, 2011, 7, pp. 5150-5160 and Jaishankar, A., Sharma, V., McKinley, G. H., "Interfacial Viscoelasticity, Yielding and Creep Ringing of Globular Protein-Surfactant Mixtures," 2011, 7, pp. 7623-7634.

Figure 4:
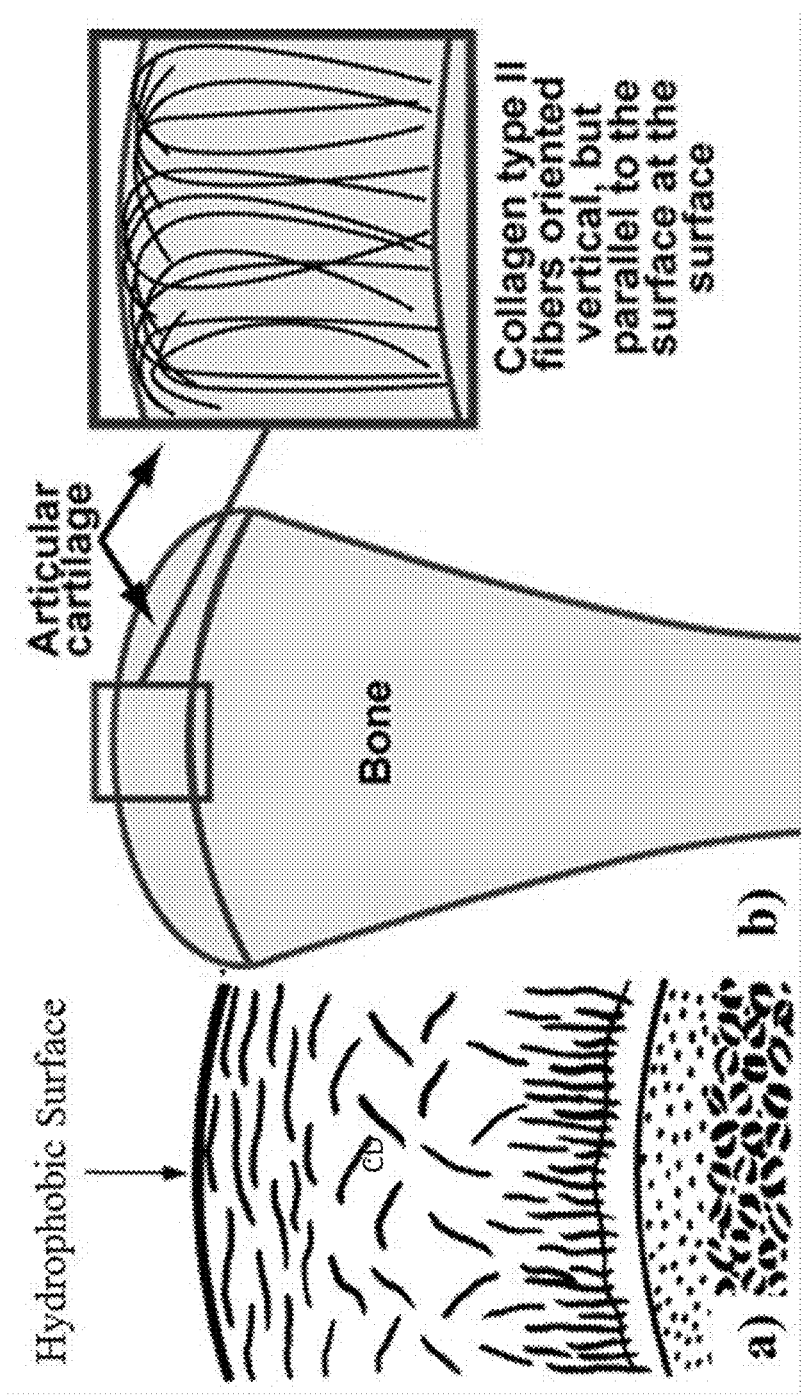
FIG. 4(a) shows a sketch of collagen fibers in an articular cartilage adjacent to bone and FIG. 4(b) shows a sketch of collagen fibers across a cartilage layer, oriented in line with the nominal direction of maximum stress.

FIG. 4 is a sketch illustrating collagen fiber orientation. Cancellous bone, which supports vertically-oriented collagen fibers, can be seen near the bottom of FIG. 4(*a*). At the hydrophobic surface, the fibers are oriented in the nominal direction of greatest stress (horizontal). FIG. 4(*b*) shows how longer collagen fibers orient themselves near underlying bone, and the surface. Lubrication and synovial fluid flow during joint motion is incredibly complex as discussed in Gleghorn, J. P., Bonassar, L. J., "Lubrication Mode Analysis of Articular Cartilage Using Stribeck Surfaces," Journal of Biomechanics, 2008, Vol. 41, pp. 1910-1918; Buschmann, M. D., Grodzinsky, A. J., "A Molecular Model of Proteoglycan-Associated Electrostatic Forces in Cartilage Mechanics," ASME Journal of Biomechanical Engineering, May 1995, Vol. 117; pp. 179-192; Eisenberg, S. R., Grodzinsky, A. J., "Swelling of Articular Cartilage and Other Connective Tissues: Electromechanochemical Forces," Journal of Orthopaedic Research, Vol. 3:2; pp. 148-159, 1985; and Schmidt, T. A., Sah, R. L., "Effect of synovial fluid on boundary lubrication of articular cartilage," Osteoarthritis and Cartilage, 15:1, pp. 25-47, 2007.

The lubrication of cartilaginous joints initially begins as hydrostatic and hydrodynamic, during motion. When motion stops, the joint settles and fluid eventually gets squeezed out of the contact patch; cartilage is different from metal in that it is deformable and permeable to synovial fluid. Boundary lubrication then becomes the dominant mode of lubrication as fluid support decreases and the fluid is squeezed out. There are also significant molecular forces that help support compressive loads in the synovial joint, such as the electrostatic repulsion of glycosaminoglycans embedded in the extracellular matrix of articular cartilage. Porous coatings could be used to create an "artificial cartilage" through fluid encapsulation. Shear-thinning synovial fluid, which is water based, could then create self-induced shear thinning flow patterns similar to core flows, as discussed in Bannwart, A. C., Rodriguez, O. M. H., De Carvalho, C. H. M., Wang, I. S., Vara, R. M. O., "Flow Patterns in Heavy Crude Oil-Water Flow," ASME Journal of Energy Resources and Technology, 126:3, pp. 184-189, 2004. Local decreases in friction could lead to formation of a single-fluid core flow, where the outer layers of the fluid are encapsulated and shear-thinning, while the core of the flow remains at a higher viscosity.

Certain embodiments relate to improvements to lubricity through the use of two similar nano-engineered (or micro-engineered) hydrophilic coatings using principles of tribology and rheology. Certain embodiments relate to modifying the surface chemistry of a material to improve wettability, causing the surface to encapsulate synovial fluid, and leading to the presence of more mixed or elasto-hydrodynamic lubrication regimes. Certain embodiments also relate to increasing the hydrophilicity of the surface to support adsorption of normal synovial fluid proteins, and to prevent adsorption of denatured proteins. As discussed above, adsorption of denatured proteins has been shown to have significant negative effects on lubricity, as discussed for example in Heuberger, M. P., Widmer, M. R., Zobeley, E., Glockshuber, R., Spencer, N. D., "Protein-mediated boundary lubrication in arthroplasty," Biomaterials, 26:1165-1173, 2005; and Roba, M., Naka, M., Gautier, E., Spencer, N. D., Crockett, R., "The Adsorption and Lubrication Behavior of Synovial Fluid Proteins and Glycoproteins on the Bearing-Surface Materials of Hip Replacements," Biomaterials, 30:2072-2078, 2009.

Figures 5A, 5B:
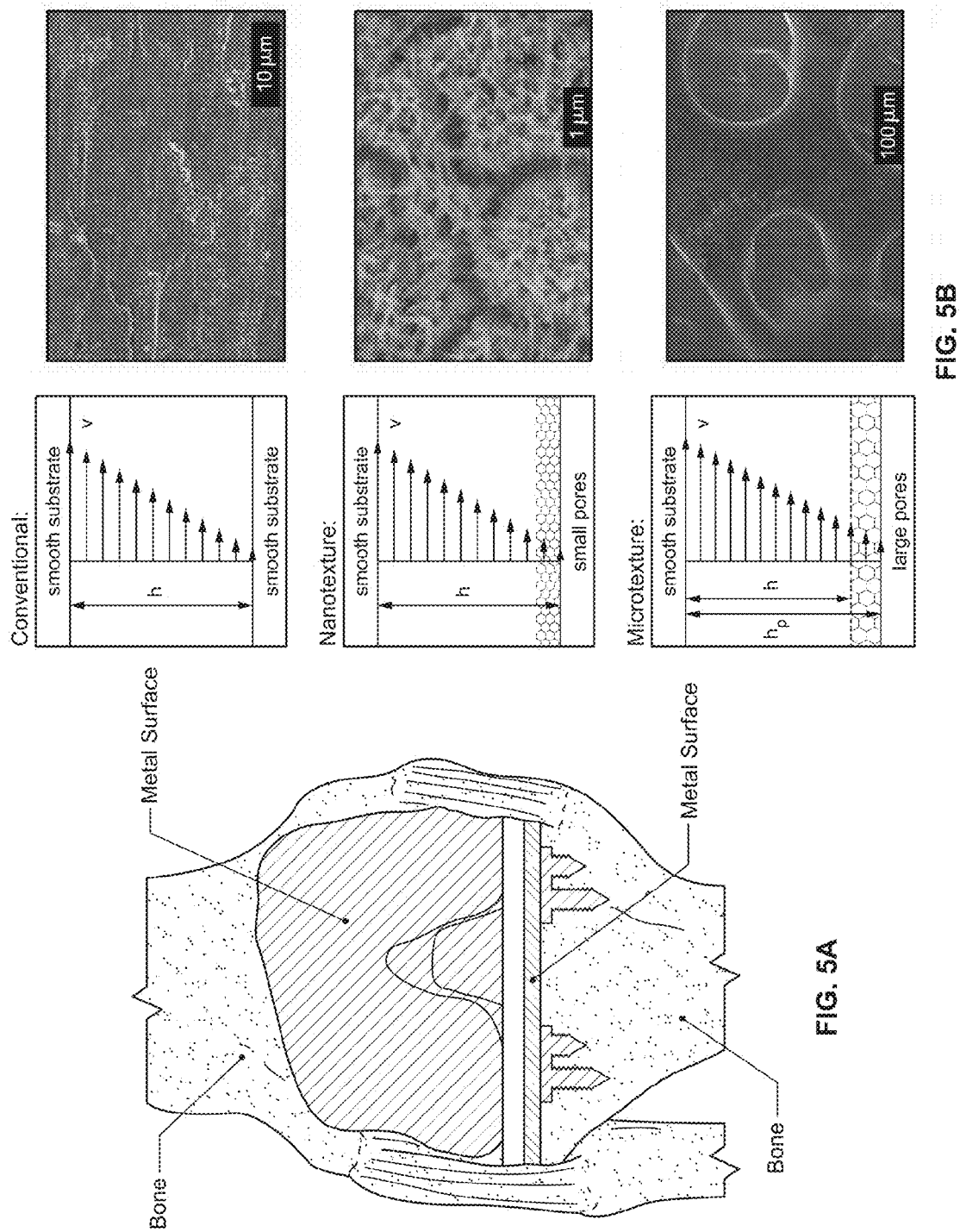
FIG. 5(a) is a schematic of lubrication between two surfaces.
FIG. 5(b) shows a series of SEM images of a prosthetic joint surface for a standard polished metal surface (top image); nano-textured surface for fluid encapsulation (middle); and micro-textured fluid for fluid encapsulation (bottom image).

FIG. 5(a) shows a schematic of lubrication between two surfaces. FIG. 5(b) shows a schematic of the proposed flow profile; by adding a porous encapsulating surface to the system, the no-slip boundary condition is eliminated at the lower boundary, and fluid encapsulation ensures that only hydrophilic native proteins adsorb onto the surface. This is analogous to the way in which water is used to create core flows in the transport of viscous heavy oils in the petroleum industry, as discussed in Bannwart, A. C., Rodriguez, O. M. H., De Carvalho, C. H. M., Wang, I. S., Vara, R. M. O., "Flow Patterns in Heavy Crude Oil-Water Flow," ASME Journal of Energy Resources and Technology, 126:3, pp. 184-189, 2004.

Grade 5 titanium alloy (Ti-6Al-4V) was used as the primary material for tribo-rheological tests. Other suitable materials used for prosthetic joints, including Cobalt Chrome, may be used as well. In some embodiments, the implant component and/or the implant component surface may be composed of or manufactured from materials, including but not limited, to UHMWPE, crosslinked UHMWPE, Zirconia, Alumina, Cobalt Chrome, Molybdenum, and any combination thereof. In some embodiments, the implant component and/or the implant component surface may be composed of or manufactured from UHMWPE/zirconia, Cobalt Chrome/Cobalt Chrome, Alumina/Alumina, Alumina/UHMWPE, Alumina/crosslinked UHMWPE, CoCrMo/CoCr/Mo, and any combination thereof. In some embodiments, the implant component and/or the implant component surface may be composed of or manufactured from metals, including but not limited to, Stainless Steel, Co—Cr—Mo, CPTi, Ti-6Al-4V, Ti-5Al-2.5Fe, Ni—Ti (e.g., 55% Ni, 45% Ti), and any combination thereof. In some embodiments, the implant component and/or the implant component surface may be composed of or manufactured from alloys, including but not limited to, Ti—Zr, Ti-6Al-4V, Ti-6Al-7Nb, Ti-5Al-2.5Fe, Ti-3Al-2.5V, Ti-13Nb-13Zr, Ti-15Mo-5Zr-3Al, Ti-12Mo-6Zr-2Fe, Ti-15Mo-2.8Nb-3Al, Ti-35Nb-5Ta-7Zr(TNZT), Ti-15Mo-2.8Nb-0.2Si-0.3O, Ti-35Nb-5Ta-7Zr-0.4O, Ti-15Mo, Ti-16Nb-10Hf, CPTi (>>98% Ti), Co—Cr—Mo, Co—Cr alloys, Stainless Steel 316L, and any combination thereof. In some embodiments, the implant component and/or the implant component surface may be composed of or manufactured from ceramic materials, including but not limited to, Zirconia, Alumina, Bioglass, C (graphite), C (vitreous), C (low-temperature isotropic carbon (ULTI), Hydroxyapatite, Apatite-Wollastonite (AW) glass ceramic, and any combination thereof. In some embodiments, at least one or both of the implant components may be composed of or manufactured from a suitable metal, polymer, ceramic, and/or any of the materials listed above. The implant components may be composed of or manufactured from the same or different materials or combinations of materials.

Starting with observations of fluid drainage in micro-textured surfaces, discussed in Seiwert, J., Maleki, M., Clanet, C., Quere, D., "Drainage on a Rough Surface," EPL, 94:16002, 2011, a model for lubrication with nano- and micro-textured surfaces can be postulated with an effective fluid viscosity $\eta_{eff}=\alpha\eta$. The factor $\alpha$ is a function of the porosity, defined by $\alpha \sim 1+h^2/d^2$, where h is often taken to be the length, and d the diameter, of the spicules making up the porous structure. The effective viscosity of a fluid flowing through the nano-texture or micro-texture would be larger than the normal viscosity of the fluid; for an equivalent gap height H; however, the coating changes the couette flow boundary conditions at the interface between the free flow $v_f$ and that through the porous medium $v_p$, through fluid encapsulation. In a lubricated system with one smooth surface and one textured surface, there are three boundary conditions: 1) the no-slip condition at the bottom of the porous coating ($v_p=0$), 2) the equal-stress condition at the boundary between the porous and free flows ($\eta_{eff} dv_p/dy=\eta dv_f/dy$), and 3) the no-slip condition at the smooth contact ($v_f=\Omega$), but there is no free surface as in previous analyses, as discussed for example in Seiwert, J., Maleki, M., Clanet, C., Quere, D., "Drainage on a Rough Surface," EPL, 94:16002, 2011.

Figure 6:
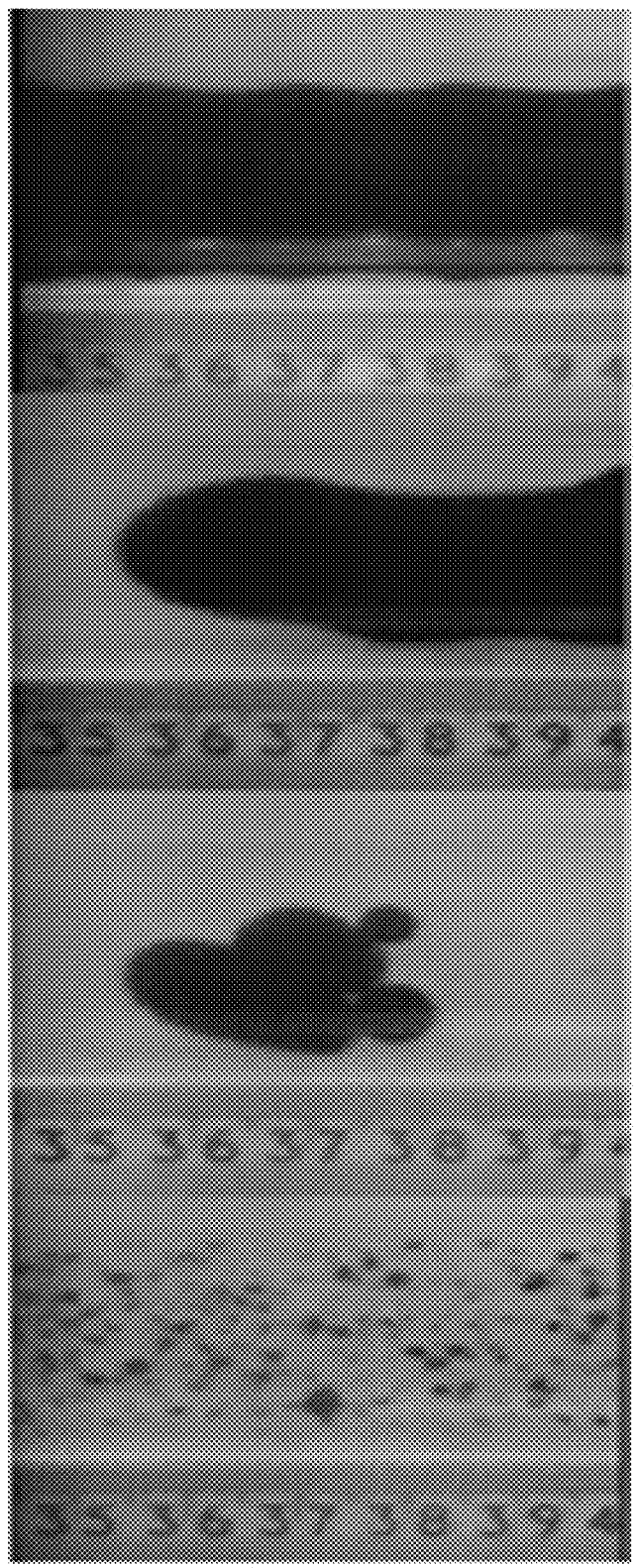
FIG. 6 shows a series of experimental images of oil core flows from Bannwart et al.: "Bannwart, A. C., Rodriguez, O. M. H., De Carvalho, C. H. M., Wang, I. S., Vara, R. M. O., "Flow Patterns in Heavy Crude Oil-Water Flow." ASME Journal of Energy Resources and Technology, 126:3, pp. 184-189, 2004."

Core flows shown in FIG. 6 are demonstrative of analogous flow conditions present in the lubricated contact; a low viscosity fluid (water) is used to transport a high viscosity fluid (crude oil). The need for a single-fluid core flow system becomes apparent when considering the risks associated with having an implant that has been impregnated with a non-renewable fluid. In certain embodiments, the non-renewable fluid is selected from, but not limited to, blood, semen, CSF, plasma, blood products, sebum, sweat, saliva, mucous secretions, bile, and other bodily fluids. Other embodiments relate to systems where the encapsulated liquid is replenished; for example, the area surrounding the implant could be connected to a reservoir containing replenishing liquid, and the replenishing liquid could be introduced into the patient via, e.g., a tube. Certain embodiments relate to use of a textured coating, which allows for the use of a single fluid (e.g., synovial fluid or other suitable fluids, as discussed above) to achieve a modified boundary condition between essentially two fluids (defined by their viscosities). In the core flow case, the two fluids are oil and water, in this case the two "fluids" are the free flow and that flowing through the porous coating (where both the free flow fluid and the fluid flowing through the porous coating are identical, e.g., synovial fluid), which necessitates the use of a shear-thinning lubricant like synovial fluid to achieve a different viscosity using the same initial fluid.

The second boundary condition (the first being that at the base of the porous media) is significantly modified when shear-thinning lubricants, like synovial fluid or serum albumin, are used. An equation for shear-dependence of viscosity was given by Kavehpour (Kavehpour, H. P., McKinley, G. H., "Triborheometry from Gap-Dependent Rheology to Tribology," Trib. Lett., 17:2, pp. 327-336, 2004) to be:

$$\eta(\dot{\gamma}_R) = \frac{T}{2\pi R^3 \dot{\gamma}_R}\left(3 + \frac{d\ln\left(\frac{T}{2\pi R^3 \dot{\gamma}_R}\right)}{d\ln \dot{\gamma}_R}\right) \quad (1)$$

From this, the equal-stress boundary condition can be modified as $\alpha\eta(\dot{\gamma}_R)dv_p/dy=\eta(\dot{\gamma}_R)dv_f/dy$. Now, because the shear in the encapsulated fluid and the free-flowing fluid, is equal just at the interface, the viscosity of the shear-dependent fluid will be equal to that of the fluid in the gap, and the viscosity term can be eliminated. This yields Equation 2 below, which relates the porosity to a ratio of the gradient of velocity in the porous flow and the flow in the gap:

$$\alpha = \frac{dv_f/dy}{dv_p/dy} \quad (2)$$

The effective viscosity of the fluid in the porous medium is greater than the viscosity of the fluid in the free flow. By definition, both $\alpha$ and in turn the velocity gradient ratio given in Equation 2 must be greater than 1. While this is counter to the more uniform velocity profile in crude oil found in core flows, because the single fluid being used is shear-thinning, increased shear stress on the fluid will result in a lower viscosity. The porous coating acts to increase the effective viscosity of the encapsulated fluid, inducing shear-thinning at the edge of the free-flow, this results in an overall improved lubrication condition by decreasing the viscosity of the free-flowing fluid. Additionally, at these length scales capillary forces dominate under static loads, and prevent the encapsulated fluid from being squeezed out from between the two surfaces.

In the case of two smooth surfaces where one is stationary and one rotating, there are two boundary conditions: 1) no-slip at the stationary plate, and 2) no-shear at the rotating plate. Because of the no-slip condition, the shear stress on the bottom plate with a fluid velocity gradient of $dv_s/dy$ given by $\tau=\eta dv_s/dy$. If a shear-thinning lubricant is used, this equation becomes $\tau=\eta(\dot{\gamma})dv/dy$. A system using only smooth surfaces with a shear thinning fluid will have reduced friction at increased shear rates simply because of the nature of the lubricant. In order for the porous coatings to improve upon this, the shear stress induced at the porous/free flow boundary must be greater than the shear stress at the bottom smooth plate. The condition for improving lubrication with a porous coating is defined by Equation 3:

$$\alpha\eta(\dot{\gamma}_R)dv_p/dy=\eta(\dot{\gamma}_R)dv_f/dy>\eta(\dot{\gamma})dv_s/dy \quad (3)$$

Synovial Fluid Models and Protein Adsorption

While Kavehpour (Kavehpour, H. P., McKinley, G. H., "Triborheometry from Gap-Dependent Rheology to Tribology," Trib Lett, 17:2, pp. 327-336, 2004) proposed a model for the shear-dependence of a fluid viscosity, there have been significant efforts to develop a model for the shear-dependency of synovial fluid. Biological fluids are inherently complex, as evidenced by the behavior of organic fluids like blood, saliva, and synovial fluid. Of these lubricants, synovial fluid is of particular concern in prosthetic joint replacements. Hron (Hron, J., Malek, J., Pustejovska, P., Rajagopal, K. R., "On the Modeling of the Synovial Fluid," Advances in Tribology, Volume 2010, Article ID 104957) proposed a model for synovial fluid viscosity defined by $\eta=\eta_0\alpha\beta+\gamma|D|^2\alpha^{n(C)}$. In this equation, the parameters $\alpha$, $\beta$, $\gamma$, and n must be determined experimentally, and they are also dependent on the concentrations of the various components of the synovial fluid (albumin, lubricin, etc.). It is interesting to note that these can be affected by various disease states, age, and whether an individual has a prosthetic joint. Due to this complexity, empirical measurements of synovial fluid are used herein to determine the viscosity at a given shear rate, as provided, for example by Jaishankar, A., Sharma, V., McKinley, G. H., "Interfacial Viscoelasticity, Yielding and Creep Ringing of Globular Protein-Surfactant Mixtures," 2011, 7, pp. 7623-7634 and Mazzucco, D., McKinley, G., Scott, R. D., Spector, M., "Rheology of Joint Fluid in Total Knee Arthroplasty Patients," Journal of Orthopaedic Research, 2002, Vol. 20:1157-1163.

EXAMPLES

Sample coupons for testing were manufactured as 40 mm diameter coupons with a 6 mm central relief hole; the relief provides a place to mount the coupons using a dowel pin for tribo-rheological experiments, as well as to ensure a non-zero minimum radius for the fluid flow. The coupons were roughed out by laser cutting 3 mm Ti-6Al-4V plate and 6 mm UHMWPE plate. These were then trued up and faced off in a lathe to ensure concentricity of the central hole with outer diameter, flatness of the surfaces, and parallelism between the top and bottom surface. The metallic coupons were then polished to ensure smoothness using and polished using a buffing wheel.

Each metal coupon was placed individually in an ultrasonic bath at room temperature for 20 minutes; after cleaning the metal coupons were placed in clean covered petri dishes for storage before chemical treatment. All polymer coupons were placed in individual beakers filled with deionized water at room temperature, and the beakers were then placed in an ultrasonic bath at room temperature for 20 minutes. These were then placed in clean covered petri dishes for storage before experimentation. Porous coatings were then created on each metallic sample via two surface treatment methods: an alkaline etch (etched) and alkaline-based electrochemical anodizing (anodizing).

Figure 7:
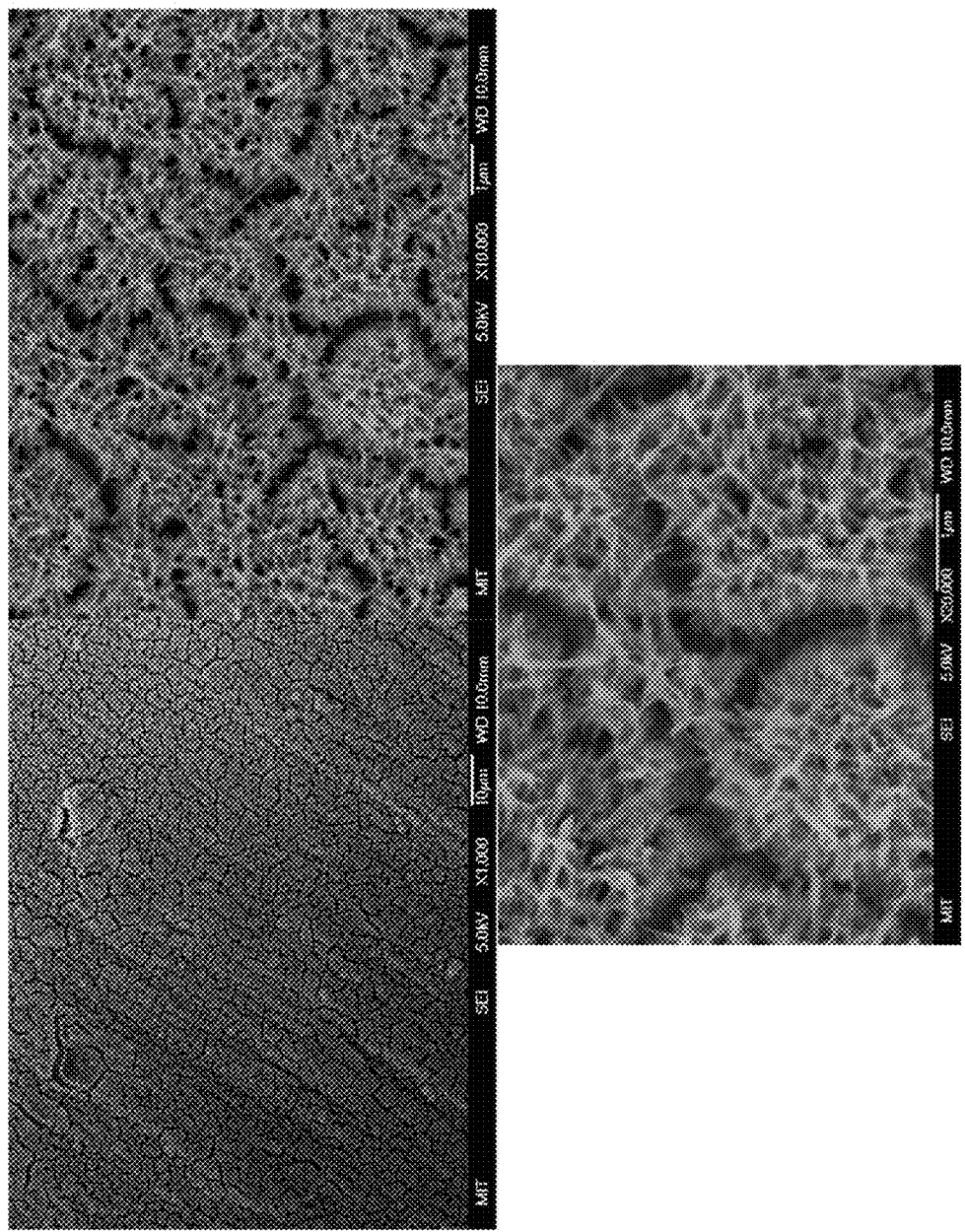
FIG. 7 shows a series of SEM images of alkaline etched samples with a sub-micron-scale porous coating at 1000× zoom.
Figure 8:
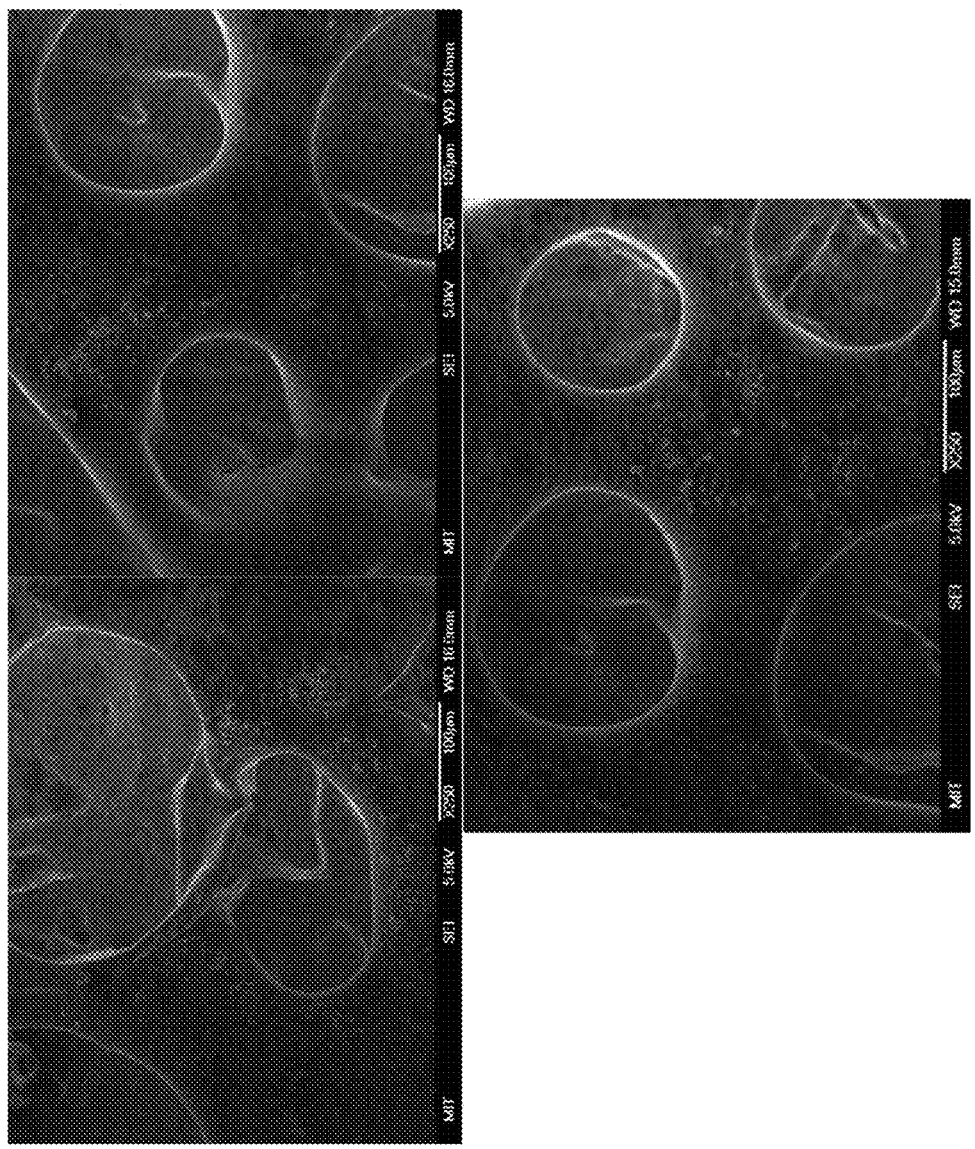
FIG. 8 shows a series of SEM images of an anodized surface coating with size on the order of one to three hundred microns at 250× zoom.

Etching consisted of placing a metal coupon in a solution of 29M NaOH at 80° C. for 29 hours, and led to the formation of nano-scale pores with a characteristic size on the order of 200-300 nm as seen in FIG. 7. Anodizing utilized 29M $H_3PO_4$ solution at 80° C. combined with 24V DC applied for the duration of a 28 hour treatment.

Figure 9:
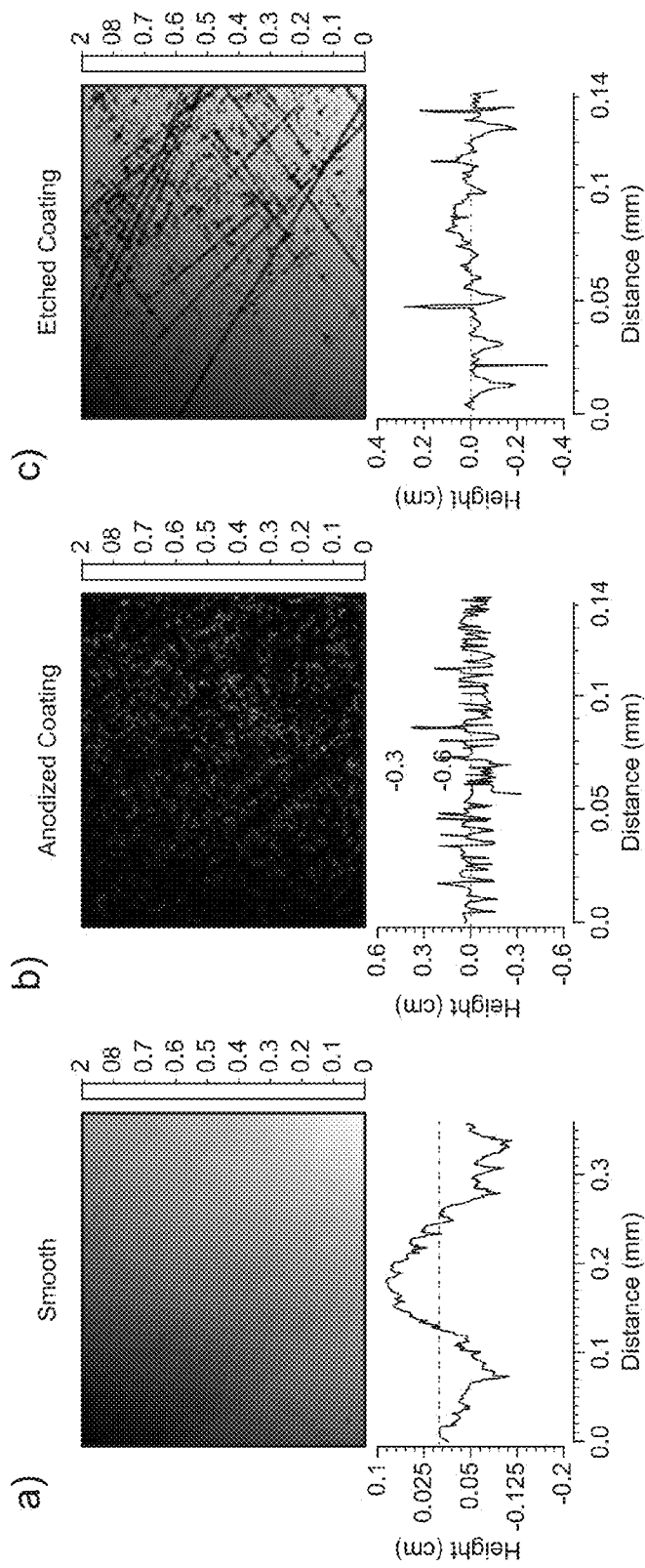
FIG. 9 shows a series of images and charts of WLI measurement of roughness of (a) polished Ti6Al4V; (b) anodized coating; and (c) etched coating.
Figure 10:
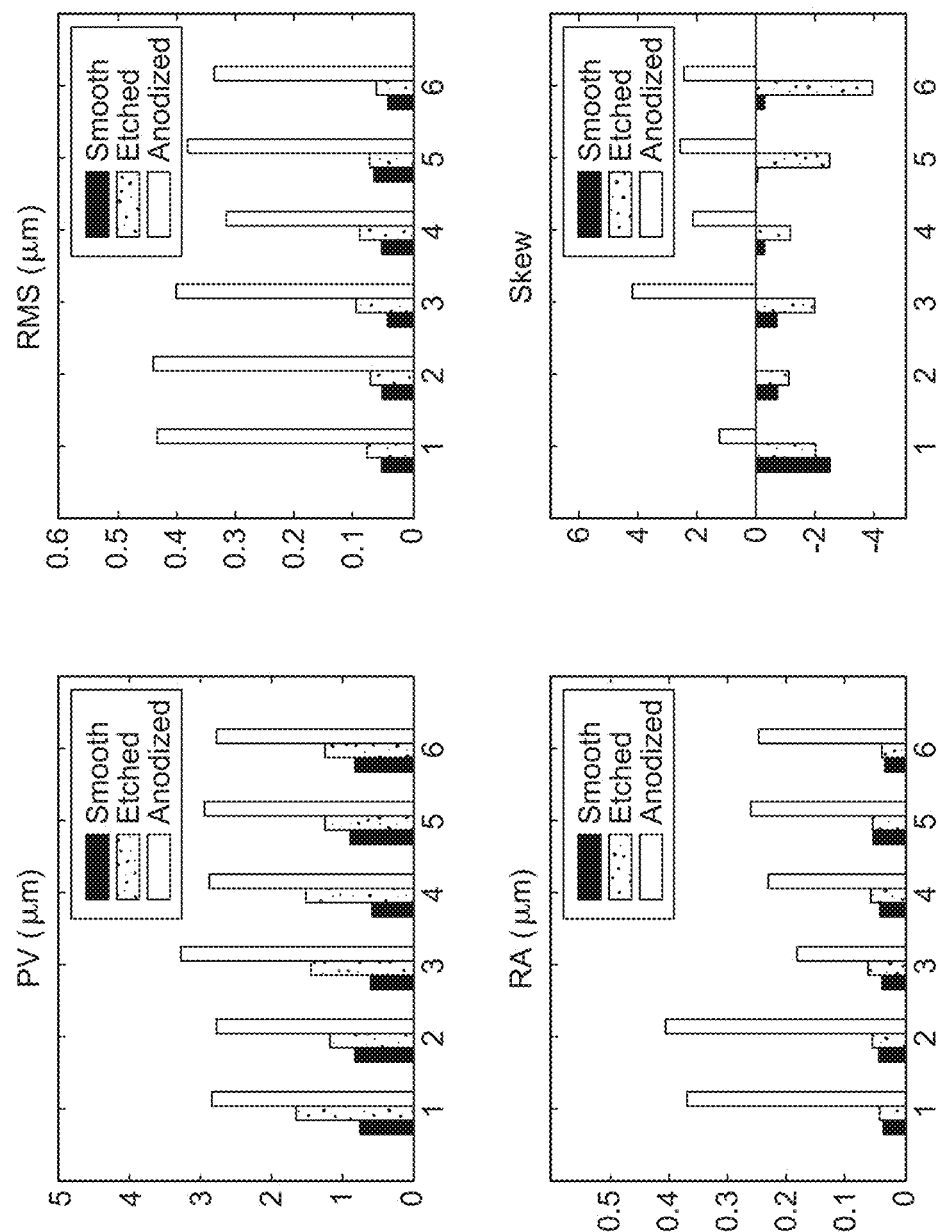
FIG. 10 shows a series of graphical representations of the surface topology of the three tested coupons, including RMS, RA, and Skew.

Surface roughness was measured for each sample (except the white UHMWPE coupons) using a white-light interferometer. For the polished coupons, mean surface roughness was approximately 50 nanometers; the etched coupons had a mean surface roughness of approximately 120 nanometers, and the anodized coupons had a mean surface roughness of approximately 200 nanometers. These measurements are summarized in Table 1. FIG. 9 and FIG. 10 show the results of white light interferometry of the smooth, anodized, and etched surfaces, including the peak-to-valley measurement (PV), RMS roughness, average roughness (RA), and the skew (RSK). The porous coatings should then, by the Wenzel equation, increase the bulk wettability and hydrophilicity of the smooth surface. Increasing the hydrophilicity of an orthopaedic metal would result in greater resistance to adsorption of denatured synovial fluid proteins, and support formation of a low-friction surface.

contact has been described previously by Kavehpour, H. P., McKinley, G. H., "Triborheometry from Gap-Dependent Rheology to Tribology," Trib Lett, 17:2, pp. 327-336, 2004; from the Couette description of flow between two rotating disks, the shear rate in the fluid is given by $\dot{\gamma}=\Omega r/H$. A feedback system in the rheometer allows for experiments to be run at either constant height, or at constant normal force (stress). In the present experiment, a constant gap height H was used, and the resultant normal force $F_N$ was recorded and used to calculate normal stress by $\sigma=AF_N$.

Starting with observations of fluid drainage in micro-textured surfaces, discussed for example in Seiwert, J., Maleki, M., Clanet, C., Quere, D., "Drainage on a Rough Surface," EPL, 94:16002, 2011, a model for lubrication with nano-textured surfaces can be postulated. The effective viscosity of a fluid flowing through the nano-texture would be larger than the normal viscosity of the fluid; for an equivalent gap height h, however, the coating eliminates the zero-slip condition present in normal couette flow at the solid surface, by encapsulating a fluid within its porous structure. An analogous situation of oil core flows used to transport high-viscosity crude is demonstrative of the conditions present. Using the principle of reciprocity, in certain embodiments, the system may be limited to impregnation of a single fluid—thus impregnation of the nano-texture will eliminate the no-slip boundary condition and result in lower friction. In some embodiments, several biological fluids (or synthetics) may be impregnated into the textured prosthetic joint surface, which could be useful for, e.g., separation of biological fluids that are mixed together. Additionally, at these length scales capillary forces dominate under static

TABLE 1

Characterization of three different surface treatments (smooth, etched, anodized).

|  | PV | RMS | RA | RSK |
|---|---|---|---|---|
| Smooth | 2.913 +/− 0.084 | 0.385 +/− 0.021 | 0.280 +/− 0.035 | 2.114 +/− 0.583 |
| Anodized | 1.360 +/− 0.075 | 0.074 +/− 0.004 | 0.046 +/− 0.003 | −2.139 +/− 0.445 |
| Etched | 0.732 +/− 0.051 | 0.048 +/− 0.003 | 0.038 +/− 0.003 | −0.805 +/− 0.378 |

Surface skew, defined as the "ratio of the third moment of the amplitude distribution and the standard deviation σ from the mean line draw through the surface roughness measurements," is also significant to certain embodiments. In physical terms, skew describes whether there are more peaks or more valleys in a surface, and a negative value implies there are more valleys than peaks. Two surfaces with equal RMS roughness can have different skew, and negative skew is beneficial for surfaces in lubricated contact. In some embodiments, the surface of the prosthetic joint has negative skew (skew having a value less than zero). More peaks increases the risk of asperity contact between two surfaces, while more valleys increases the space for fluid encapsulation, as discussed in, Hupp, S. J., Hart, D. P., "Experimental Method for Frictional Characterization of Micro-Textured Surfaces," Proceedings of the 2004 ASME/STLE International Joint Tribology Conference, Long Beach, Calif., Oct. 24-27, 2004.

Roughness directly affects flow in a lubricated contact, and is an important characteristic of these systems which must be considered, along with typical design considerations for sliding contact bearings as discussed in Slocum, A. H., "Precision Machine Design" (1992), Prentice Hall, Englewood Cliffs, N.J., pp. 425-444. Flow in the lubricated loading conditions and prevent fluid from being squeezed out from between the two surfaces.

Surface Wetting

Figure 11:
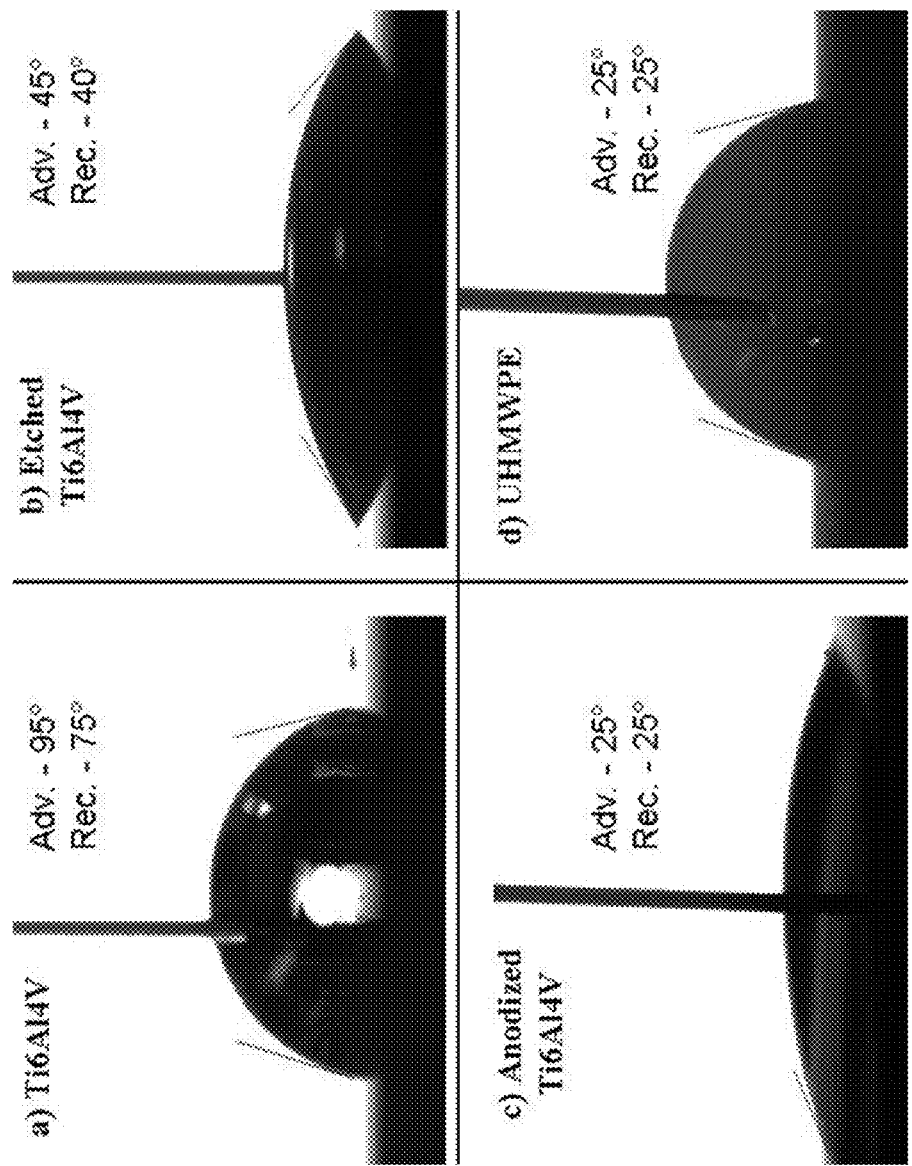
FIG. 11 shows a series of experimental contact angle measurement images for (a) smooth Ti6Al4V; (b) etched Ti6Al4V; (c) anodized Ti6Al4V; and (d) UHMWPE.
Figure 12:
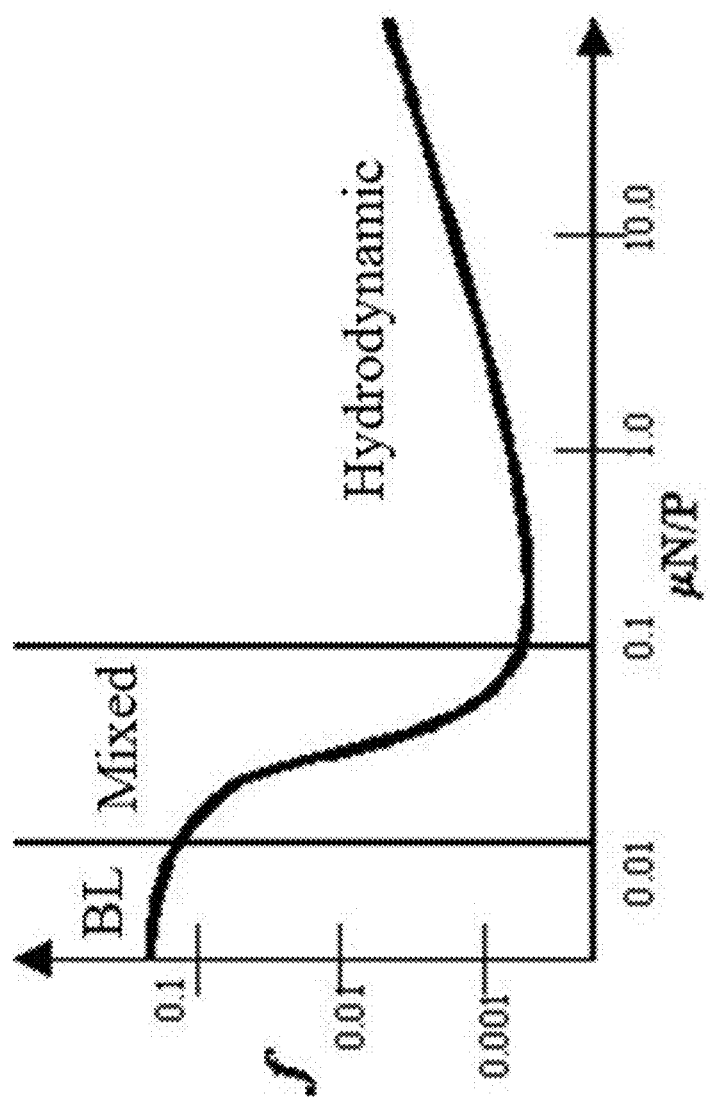
FIG. 12 shows a Stribeck diagram highlighting the three lubrication regimes, the relationship between friction coefficient (f) and Stribeck number, and how this can be used to identify the presence of a specific regime.

Hydrophilicity of each surface was measured by tracking the advancing and retreating contact angle of a droplet using a Rame-Hart Model 500 Advanced Goniometer with DROPimage Advance v2.4 software (Ramé-Hart, Succasunna, N.J.) and deionized water (DIW). Each sample was placed on the goniometer platform and a contact angle was measured multiple times with a 6 µL droplet. Contact angle images can be seen in FIG. 11; the contact angles for each surface are given in Table 2 below. From these measurements it can be observed that by creating a porous coating in the smooth titanium surface, its wetting characteristics can be significantly improved. Certain embodiments relate to prosthetic joint surfaces having a contact angle (with water) of less than or equal to 50°, less than or equal to 40°, less than or equal to 30°, or less than or equal to 25°. In comparison, the contact angle with water on a smooth surface is typically between 80-120°. Porous prosthetic joint surfaces having a maximum contact angle with water of 50° (or those surfaces having a contact angle with water of less than 50°) have a significantly better ability to draw water (or other fluids) into the porous coating as opposed to smooth prosthetic joint surfaces. Water is used as a reference fluid since properties of water are well-known, and properties of biological fluids vary to a great extent among individuals. Those of ordinary skill in the art would appreciate that a porous surface having a contact angle of less than 50° with water (and thus having significantly better ability to draw water into the surface) would similarly have a much better ability to draw biological fluids (such as synovial fluid) into the surface as compared to those smooth surfaces having a contact angle with water of between 80-120°.

TABLE 2

Summary of contact angles on different surfaces.

| Material | Advancing Contact Angle | Retreating Contact Angle |
| --- | --- | --- |
| Smooth Ti | 95° | 75° |
| Anodized Ti | 25° | 25° |
| Etched Ti | 45° | 40° |
| UHMWPE | 100° | 50° |

Tribo-Rheology of Nano-Engineered Surfaces

Rheology is the study of fluid flow and viscosity, while tribology is the study of friction and wear in a lubricated contact. Tribo-rheology utilizes a rheometer to study the characteristics of a contact pairing lubricated by a given fluid, as discussed in Kavehpour, H. P., McKinley, G. H., "Triborheometry from Gap-Dependent Rheology to Tribology," Trib Lett, 17:2, pp. 327-336, 2004. Typically, a Stribeck plot is used to describe a lubricated contact; it gives the measured friction coefficient versus a non-dimensional velocity termed the Stribeck number. The Stribeck number is equal to the product of viscosity and rotational velocity, divided by normal stress; linearity in the plot is typically interpreted as an indication of the presence of hydrodynamic lubrication.

Bovine Synovial Fluid (BSF, Lampire Biological Laboratories, Pipersville, Pa.), deionized water (DIW), and Silicone Oil (SO) were obtained for use in lubricating the coupons. Tribo-rheological characteristics of the system were assessed in an AR-2 Rheometer (TA Instruments, New Castle, Del.) using a plate-on-plate configuration. Tribological characteristics of the interface are determined based on previous methods described by Kavehpour, H. P., McKinley, G. H., "Triborheometry from Gap-Dependent Rheology to Tribology," Trib Lett, 17:2, pp. 327-336, 2004. Tribo-rheological testing of 7 different surface configurations was performed using different fluids: deionized water ($\mu_w$=1E-3 cSt), silicone oil ($\mu_o$=50E-3 cSt), and bovine synovial fluid ($\mu_s$). Four experiments were used to generate Stribeck curves for a lubricated contact, wherein the lubricant fluid was compressed between two coupons: smooth-smooth, smooth-etched, smooth-anodized, and etched-anodized.

"Smooth" refers to a polished coupon that has not had any chemical surface treatment besides being polished and cleaned, "etched" refers to a coupon subsequently treated with alkaline etching, and "anodized" refers to a coupon treated with alkaline anodization after cleaning. The same sequence of tests were performed, including range of shear rates, using deionized water (a Newtonian fluid) as a lubricant to provide a baseline of comparison for the synovial fluid tests. Any coating applied to a surface in an attempt to improve lubrication must serve two purposes: 1) it must produce either an equivalent or lower coefficient of friction as conventional implant surfaces, and 2) it must encapsulate the fluid in order that lubricant (in this case, synovial fluid) is not squeezed out from between the components, in order to prevent touch down or asperity contact.

Determination of the coefficient of friction for a given system consisting of a pair of surfaces and an intervening lubricant was based on previous work by Kavehpour, H. P., McKinley, G. H., "Triborheometry from Gap-Dependent Rheology to Tribology," Trib Lett, 17:2, pp. 327-336, 2004, using the same AR-2 rheometer (TA instruments, New Castle, Del.). Because two different surfaces need to be pre-fabricated, and different pairings of coatings on surfaces are required to evaluate the full number of potential pairings, a fixture had to be constructed so that different surfaces could be rotated against one another. A passive alignment mechanism was designed utilizing a kinematic coupling (KC) supported by flexures. This mechanism can be seen in the series of images in FIG. 13.

Figure 13:
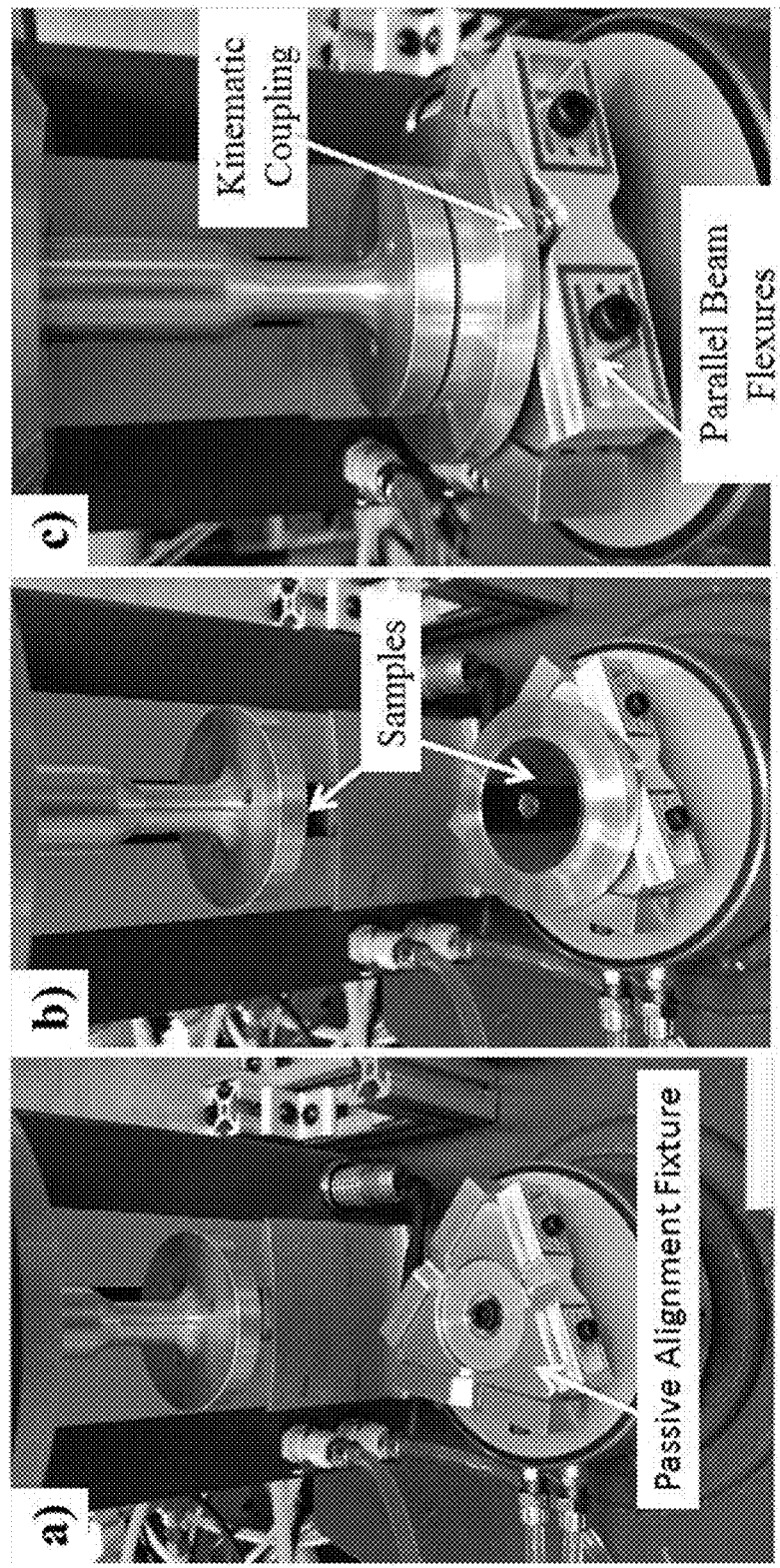
FIG. 13 shows an experimental precision passive alignment fixture designed to ensure planarity of different sample pairings during experiments.

Using the alignment fixture seen in FIG. 13, multiple experiments were run on each material pairing. Shear rate was varied between 0.01 and 1000 $s^{-1}$ for each experiment, and a constant gap height of 100 microns was used for all tests. Boundary-level effects at lower shear rates, like a higher coefficient of friction, are not expected to be seen on the Stribeck diagram in experiments where the gap height is maintained at a constant value. Below a certain shear rate, what should be boundary-layer type flow is approximated as such. Hydrodynamic lubrication is usually present at high shear-rates under steady-state conditions. Certain embodiments relate to prosthetic joints having a gap height that varies. In some embodiments, the gap height is zero microns (e.g., where contact occurs). In some embodiments, the gap height has a value anywhere within a range between about 1 micron and about 5 mm, including between 10-50 microns, 10-100 microns, 100-200 microns, 200-300 microns, 300-500 microns, 500-700 microns, 700-1000 microns, 10-1000 microns.

Figure 14:
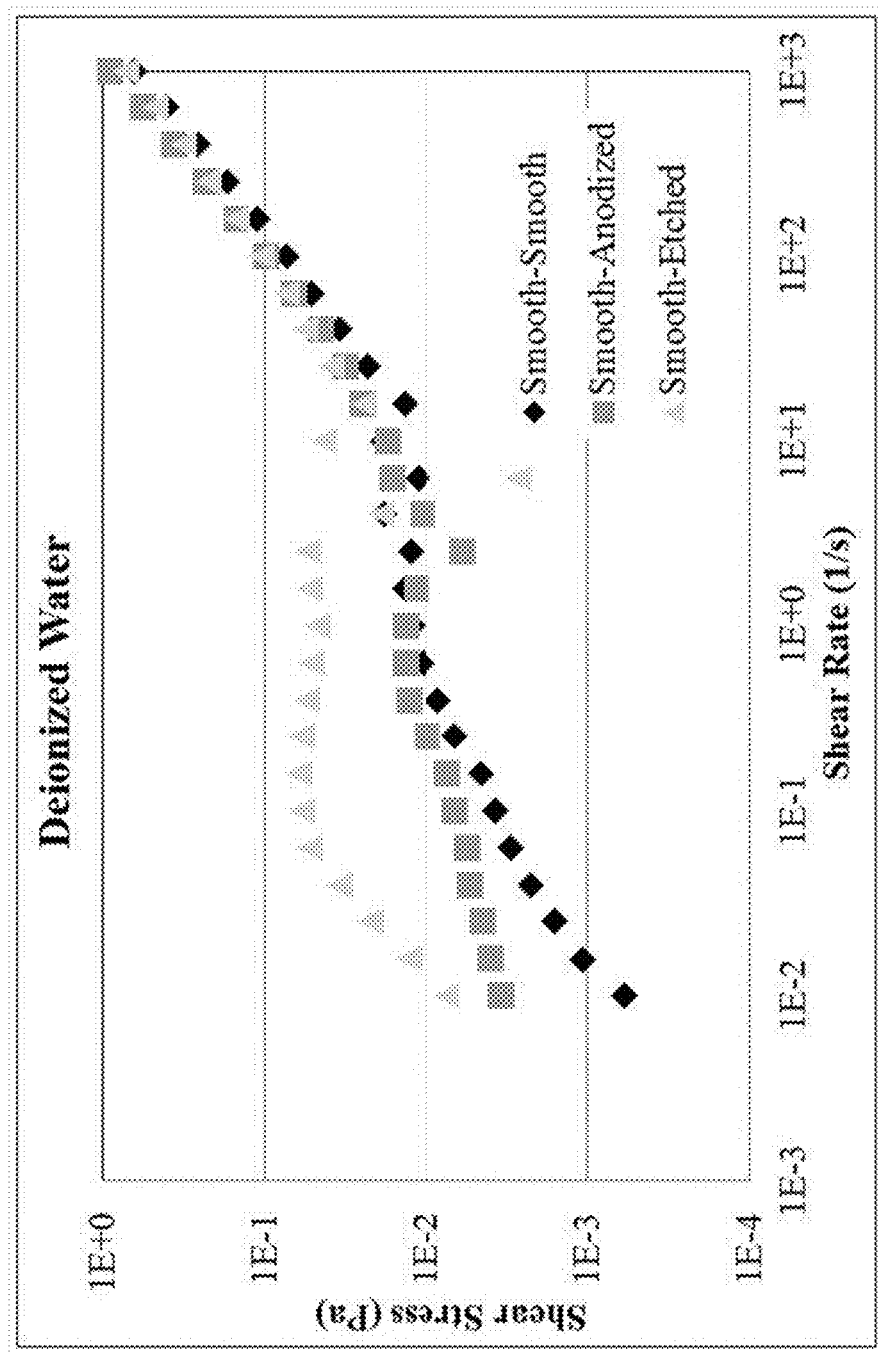
FIG. 14 shows a log-plot of shear stress versus shear rate for experiments using deionized water.

The first experiments performed involved deionized water, which acts as a control because it is a Newtonian fluid and the expected shape of the Stribeck diagram is known, as discussed for example by Hupp, S. J., Hart, D. P., "Experimental Method for Frictional Characterization of Micro-Textured Surfaces," Proceedings of the 2004 ASME/STLE International Joint Tribology Conference, Long Beach, Calif., Oct. 24-27, 2004. Plots of shear stress versus shear rate are presented first, and then Stribeck diagrams for each situation are shown. FIG. 14 shows a log-plot of shear stress versus shear rate for the case of deionized water. The slope of the linear region above a shear rate of 10 should be the viscosity of water, which is $1\times10^{-3}$; the slope of the plot in the figure is approximately $10^{-3}$, which means that the setup performs as expected.

As discussed above, synovial fluid is a visco-elastic non-Newtonian shear-thinning fluid, so no single value for kinematic viscosity is available. Synovial fluid viscosity is dependent on shear rate, control values for synovial fluid were taken from previous studies by Mazzucco, D., McKinley, G., Scott, R. D., Spector, M., "Rheology of Joint Fluid in Total Knee Arthroplasty Patients," Journal of Orthopaedic Research, 2002, Vol. 20:1157-1163, where viscosity is given as a function of shear rate for human synovial fluid. Here, the viscosity measured in the experiment measured from 6-0.01 Pa-s with increasing shear rate. Also, because synovial fluid is a non-Newtonian shear-thinning lubricant, the couette flow model of lubrication between two plates, seen in FIG. 5(b) must be modified.

Figure 15:
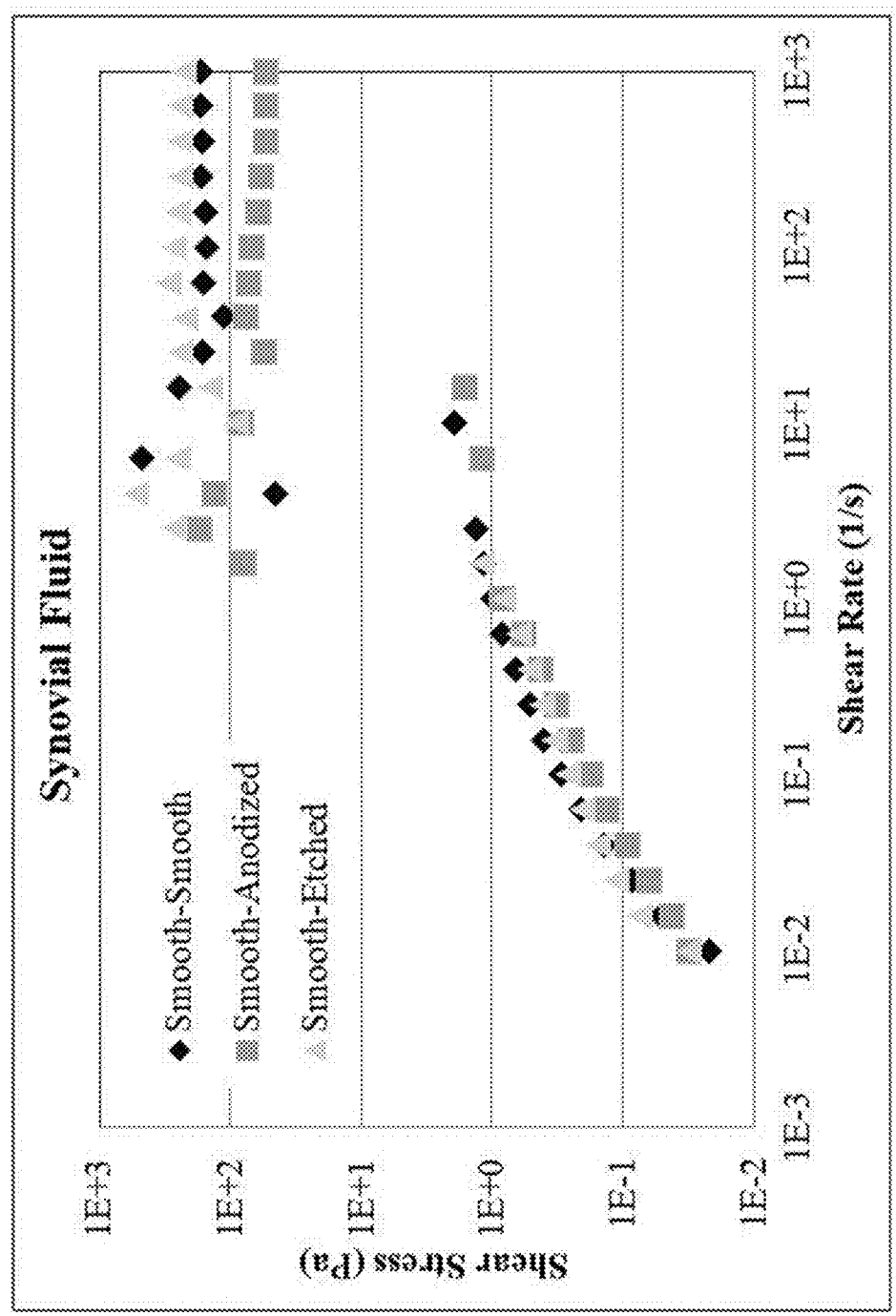
FIG. 15 shows a log-plot of shear stress for experiments using synovial fluid.
Figure 16:
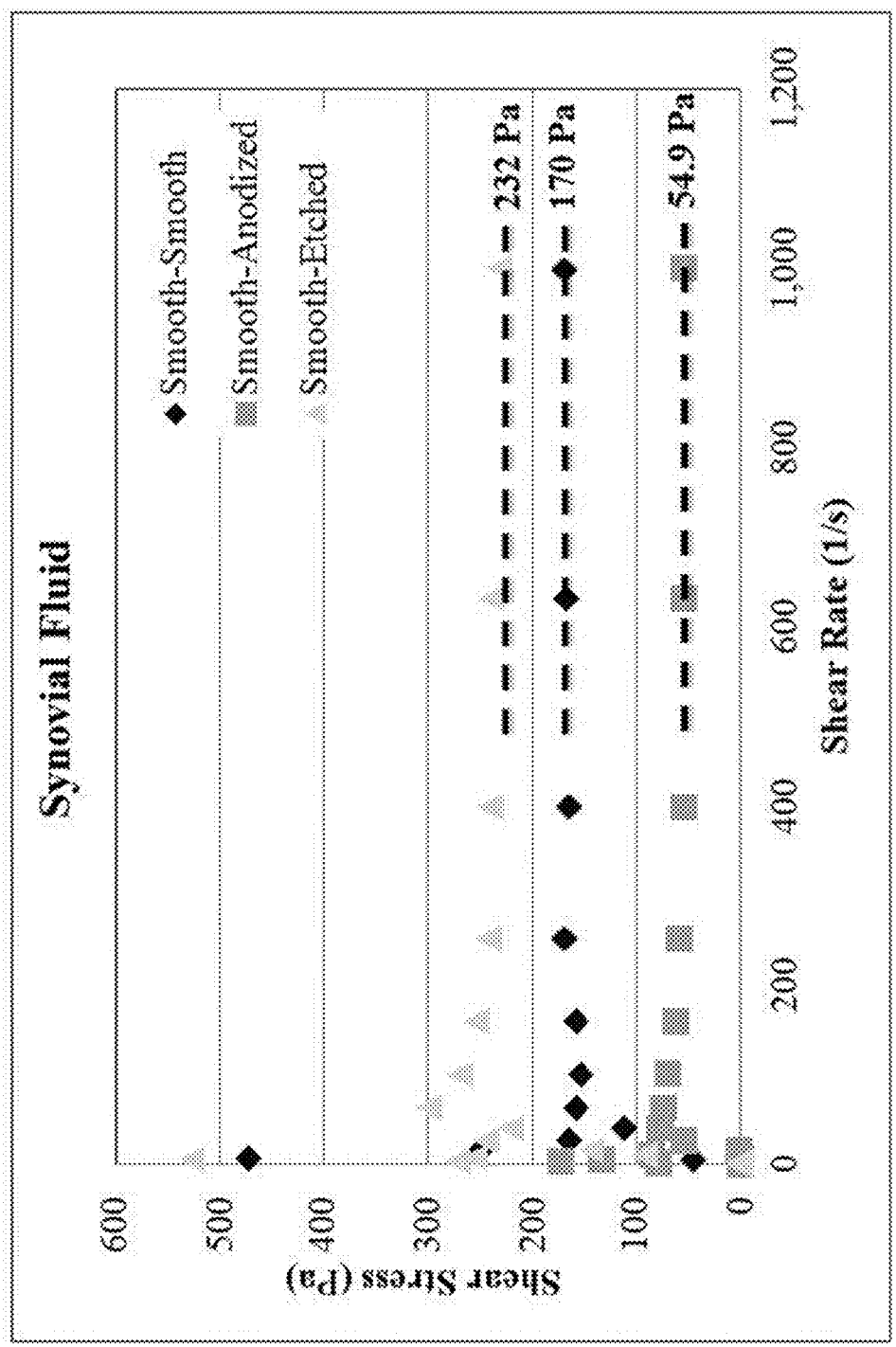
FIG. 16 shows a linear plot of shear stress versus shear rate (using the same data as shown in FIG. 15), further demonstrating the degree of shear stress reduction when an anodized coating, lubricated with synovial fluid, is in contact with a smooth surface.

FIG. 15 shows a log-plot of synovial fluid versus shear rate. At low shear rates (<1/s), the gap height would normally be determined by boundary layer lubrication, but because it is set to 100 μm for this setup, the shear stress is significantly reduced. Low-amplitude oscillations were observed during collection of data, and because of the presence of boundary layers, the surface chemistry of the smooth or coated coupon would also have an effect on the flow (whether or not it supported a stable boundary layer). At higher shear rates (above 10/s), shear-thinning of the synovial fluid is observed as the shear stress stays constant even as the shear rate increases. In FIG. 16, the anodized coating leads to a decrease in shear stress by an average of 63%.

The effects of the anodized coating can be further highlighted by plotting the data from FIG. 15 on a linear scale, as seen in FIG. 16. The value for shear stress indicated by the final data points (the steady-state operating conditions) show that the smooth-smooth sample pair experiences a shear stress of 170 Pa. When one of the components is replaced by a sample which has been anodized, the shear stress drops to below around 55 Pa, which represents a reduction in shear stress of 68%.

Figure 17:
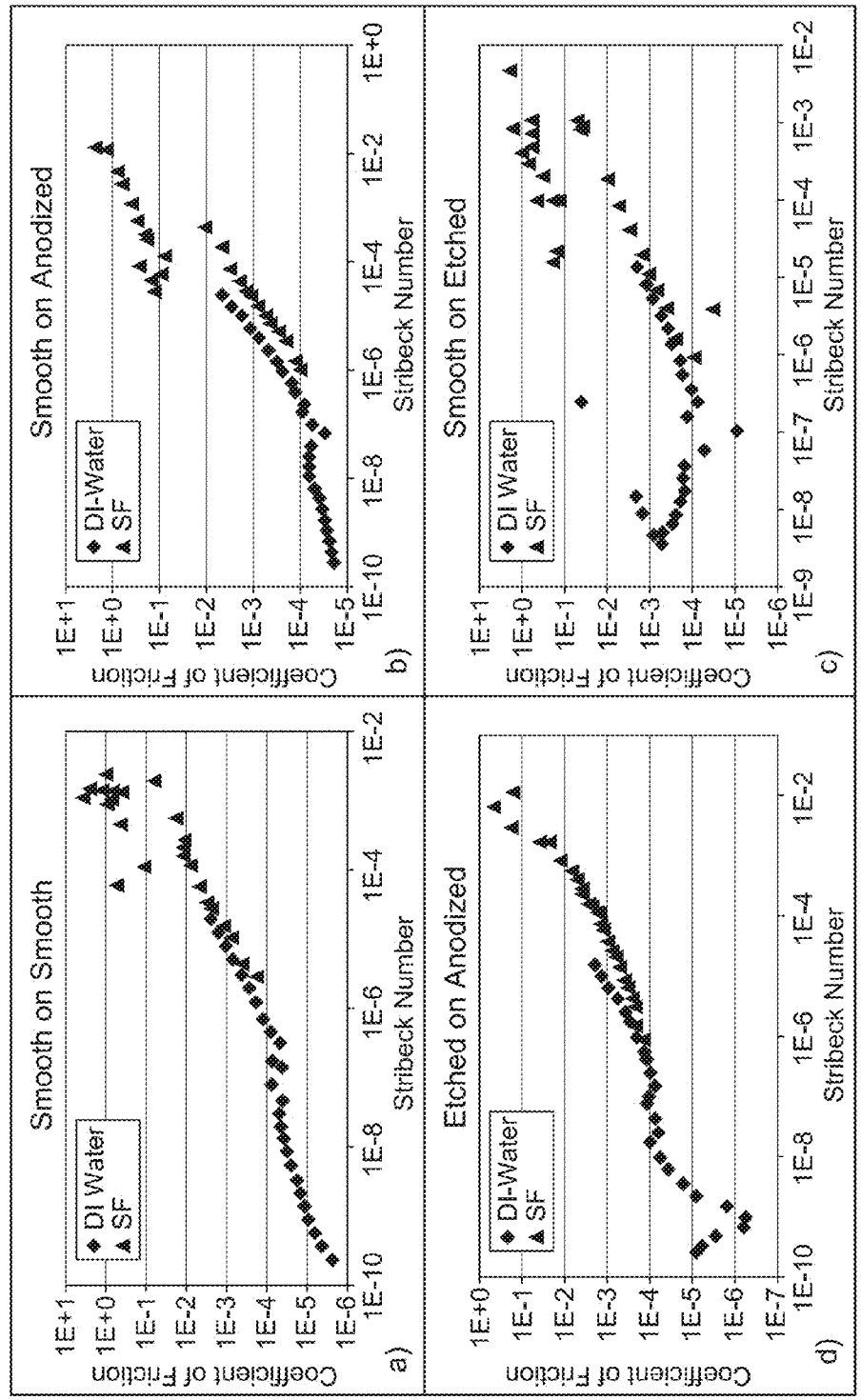
FIG. 17 shows Stribeck plots for different surface coating pairs using deionized water and synovial fluid as lubricants, including (a) smooth on smooth; (b) smooth on anodized; (c) smooth on etched; and (d) etched on anodized.

Based on observations of each experiment, sharp rises in shear stress and friction coefficient appeared between shear rates of 1 and 10 across all combinations of lubricants and contact pairs, seen in FIG. 14 and FIG. 15. It is hypothesized that this is due to resonant phenomena resulting from the compliant beams in the precision passive alignment mechanism used to ensure planarity between coupons. In FIG. 17, conditions suggesting the presence of hydrodynamic lubrication (linearity) are seen more readily when synovial fluid is used, particularly when combined with the anodized coating as in FIG. 17(*b*). In some embodiments, the hydrodynamic lubrication is maintained as long as the lubricant (e.g., synovial fluid) remains in a stable condition. The synovial fluid does not stagnate in the surface. There is a flux of synovial fluid through the gross structure over a period of time. In some embodiments, the synovial fluid (or other suitable encapsulating liquid) is encapsulated in the surface for a suitable residence time. Residence time is an average amount of time that a particle spends encapsulated within the solid features. In some embodiments, the residence time is between 1-60 seconds. In some embodiments, the residence time is less than 5 seconds, less than 10 seconds, on the order of 10 seconds, between 1-10 seconds, 10-20 seconds, 20-30 seconds, 30-40 seconds or another suitable time period.

Figure 18:
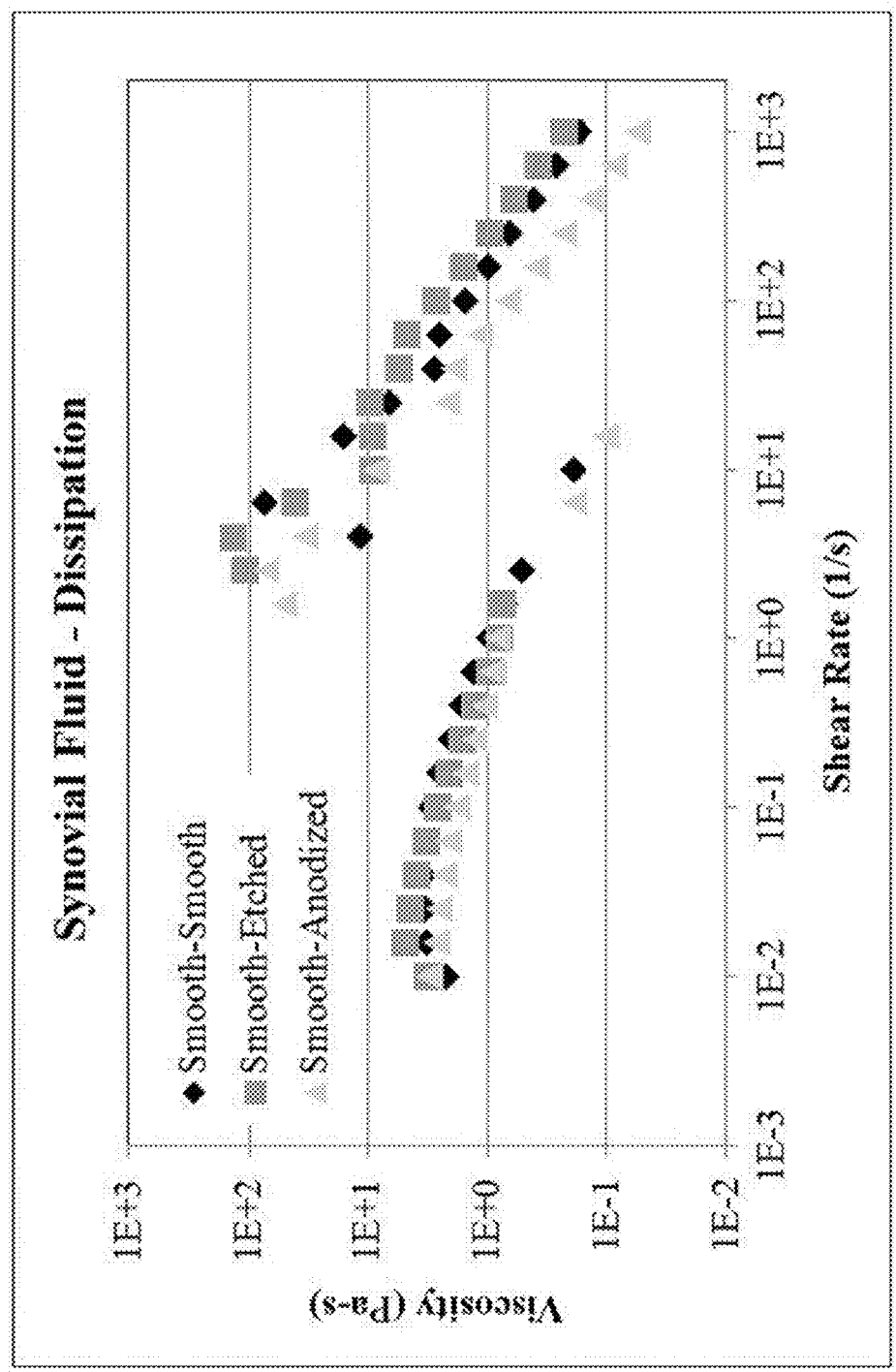
FIG. 18 shows a plot of synovial fluid dissipation for different lubricated contacts, including smooth on smooth; smooth-etched; and smooth-anodized.

Dissipation in the fluid gap can also be assessed by plotting the measured viscosity of the synovial fluid versus shear rate. Spikes in the viscosity between shear rates of 1 and 10/s are further suggestive of a resonant or other phenomena resulting from the presence of compliant flexures used in the testing apparatus and it would be apparent to those of ordinary skill in the art that their arrangement is intended to maintain planarity of samples relative to one another. These parallel flexure beams are illustrated in FIG. 13(*c*). The downward slope seen in FIG. 18 after a shear rate of 1/s is illustrative of shear-thinning, as the amount of dissipation and the anodized coating induces the greatest degree of this effect as the viscosity of the lubricant is at its lowest.

Slip Length

Figure 19:
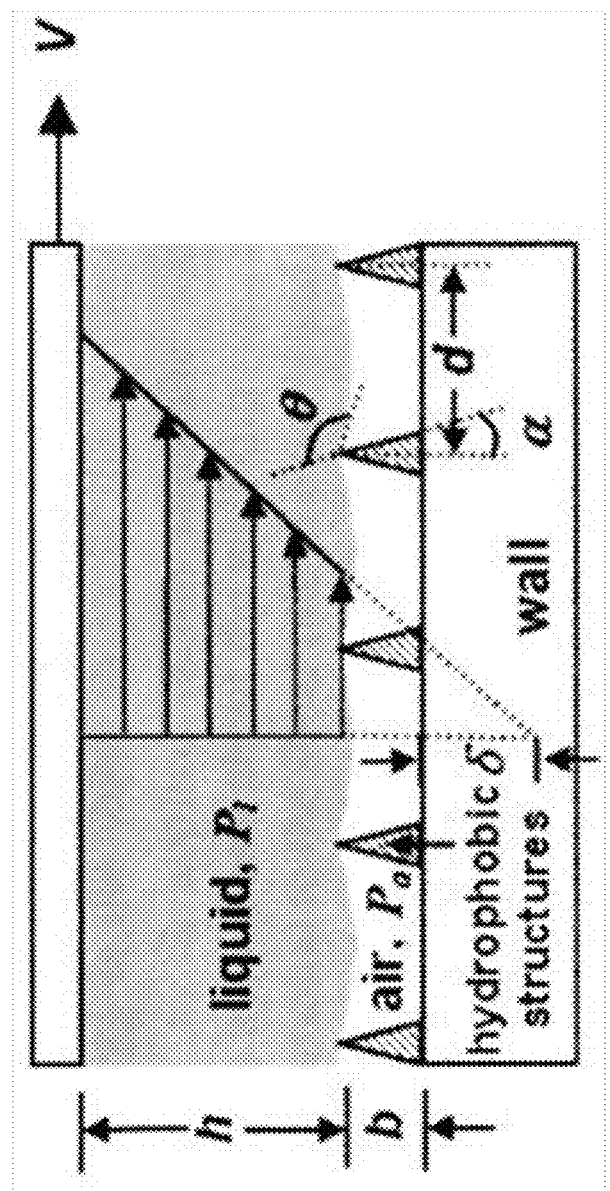
FIG. 19 shows a schematic of a micro-textured surface illustrating the concept of slip length, labeled as δ from Coi, C.-W., Kim, C.-J., "Large Slip of Aqueous Liquid Flow over a Nanoengineered Superhydrophobic Surface," PRL 96, 066001-4, 2006.

Previous experiments, such as in Coi, C.-W., Kim, C.-J., "Large Slip of Aqueous Liquid Flow over a Nanoengineered Superhydrophobic Surface," PRL 96, 066001-4, 2006 utilized an angled platen, and glycerin and water as lubricants; FIG. 19 shows a schematic of the micro textured coating impregnated with air used by Coi, C.-W., Kim, C.-J., "Large Slip of Aqueous Liquid Flow over a Nanoengineered Superhydrophobic Surface," PRL 96, 066001-4, 2006. Equation 4 provides an expression for slip length based on the shear stress at the top and bottom contacts, and used to estimate a slip length of δ=170 μm for the anodizing coating. A greater slip length indicates that the material has a greater tendency to improve lubrication and that it is easier for the lubricant (e.g., synovial fluid or other suitable lubricant) to slip over the surface. A shorter slip length indicate that it is more difficult for the lubricant to move across the surface.

$$\left(\frac{\tau_{slip}}{\tau_{no\text{-}slip}}\right)_{couette} = \frac{1}{1+(\delta/h)} \quad (4)$$

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A prosthetic joint, comprising:
a first joint component and a second joint component, the first joint component positioned in relation to the second joint component such that it is separated from the second joint component by a gap throughout a range of motion of the first joint component in relation to the second joint component, wherein the gap has a thickness that varies according to position within the range of motion of the first joint component in relation to the second joint component, wherein the first joint component comprises a first surface opposing the second joint component, the first surface having a first texture comprising solid features configured to stably contain a biological fluid or a synthetic biological fluid therebetween or therewithin for a non-zero residence time, wherein the first texture comprises micro- and nano-features, configured to encapsulate the biological fluid or the synthetic biological fluid for the residence time, wherein the micro-features have an average length of between 1-10 microns, and wherein the nano-features have an average length of between 10-500 nanometers.

2. The prosthetic joint of claim 1, wherein the biological fluid or the synthetic biological fluid is synovial fluid.

3. The prosthetic joint of claim 1, wherein the biological fluid or the synthetic biological fluid comprises at least one fluid selected from mucus, blood, blood products, saliva, lacrimal fluid, bovine serum, human serum, secretion, semen, cerebrospinal fluid (CSF), plasma, bile, bodily fluids, any biological fluid(s) including a suspended protein, and any combination of the above-mentioned fluids.

4. The prosthetic joint of claim 1, wherein the first surface has a contact angle with water of ≤50°.

5. The prosthetic joint of claim 1, wherein the first surface has a skew value of less than 0 (zero).

6. The prosthetic joint of claim 1, wherein the residence time is between 5 seconds and 40 seconds.

7. The prosthetic joint of claim 1, wherein the first texture is an etched surface, an anodized surface, or a surface treated chemically or electro-chemically to induce formation of nano- or micro-features.

8. The prosthetic joint of claim 1, wherein the second joint component comprises a second surface, the second surface opposing the first surface, the second surface having a second texture comprising solid features.

9. The prosthetic joint of claim 8, wherein the second texture is an etched surface, an anodized surface, or a surface treated chemically or electro-chemically to induce formation of nano- or micro-features.

10. The prosthetic joint of claim 8, wherein the solid features of the second texture define pores or structures capable of encapsulating fluids for the residence time.

11. The prosthetic joint of claim 1, the prosthetic joint being configured to support formation of a hydrodynamic lubrication regime and to maintain said hydrodynamic lubrication regime between the first and the second joint components.

12. The prosthetic joint of claim 1, the prosthetic joint being configured to modify the shear stress and friction between the first component and the second component to improve lubrication between the first component and the second component.

13. The prosthetic joint of claim 12, wherein the prosthetic joint is configured to reduce the shear stress by more than about 50% as compared to an analogous prosthetic joint with the first surface and the second surface being smooth.

14. The prosthetic joint of claim 1, wherein the first surface, the second surface, or the first surface and the second surface, comprise a metal, a metal alloy, a polymer, a ceramic, a metal polymer, or any combination thereof.

15. The prosthetic joint of claim 1, wherein the first surface, the second surface, or the first surface and the second surface, comprise Ti—Zr, Ti-6Al-4V, Ti-6Al-7Nb, Ti-5Al-2.5Fe, Ti-3Al-2.5V, Ti-13Nb-13Zr, Ti-15Mo-5Zr-3Al, Ti-12Mo-6Zr-2Fe, Ti-15Mo-2.8Nb-3Al, Ti-35Nb-5Ta-7Zr(TNZT), Ti-15Mo-2.8Nb-0.2Si-0.3O, Ti-35Nb-5Ta-7Zr-0.4O, Ti-15Mo, Ti-16Nb-10Hf, CPTi (>>98% Ti), Co—Cr—Mo, Co—Cr alloys, Stainless Steel 316L, and any combination thereof.

16. The prosthetic joint of claim 1, wherein the gap height is between 10 microns and 1 millimeter.

17. A prosthetic joint, comprising:
a first joint component comprising a first surface, the first surface having a first texture comprising solid features configured to stably contain a biological fluid or a synthetic biological fluid therebetween or therewithin for a non-zero residence time, wherein the first texture comprises micro- and nano-features, configured to encapsulate the biological fluid or the synthetic biological fluid for the residence time, wherein the micro-features have an average length of between 1-10 microns, and wherein the nano-features have an average length of between 10-500 nanometers.

18. The prosthetic joint of claim 17, wherein the first texture is a coating.

19. The prosthetic joint of claim 17, wherein the first texture is not a coating.

20. The prosthetic joint of claim 17, wherein the biological fluid or the synthetic biological fluid is synovial fluid.

21. The prosthetic joint of claim 17, wherein the biological fluid or the synthetic biological fluid comprises at least one fluid selected from mucus, blood, blood products, saliva, lacrimal fluid, bovine serum, human serum, secretion, semen, cerebrospinal fluid (CSF), plasma, bile, bodily fluids, any biological fluid(s) including a suspended protein, and any combination of the above-mentioned fluids.

22. The prosthetic joint of claim 1, wherein the first surface has a contact angle with water of ≤25°.

* * * * *